(12) United States Patent
Nakae et al.

(10) Patent No.: US 8,530,231 B2
(45) Date of Patent: Sep. 10, 2013

(54) VACUUM BLOOD COLLECTION TUBE

(75) Inventors: Hiroki Nakae, Tokyo (JP); Haruka Uesaka, Tokyo (JP); Atsuhiko Minekawa, Nabari (JP); Takeshi Kurono, Yamatokooriyama (JP)

(73) Assignee: Kaneka Corporation, Osaka (JP)

( * ) Notice: Subject to any disclaimer, the term of this patent is extended or adjusted under 35 U.S.C. 154(b) by 725 days.

(21) Appl. No.: 12/520,994

(22) PCT Filed: Dec. 27, 2007
(Under 37 CFR 1.47)

(86) PCT No.: PCT/JP2007/075133
§ 371 (c)(1),
(2), (4) Date: Oct. 7, 2009

(87) PCT Pub. No.: WO2008/078808
PCT Pub. Date: Jul. 3, 2008

(65) Prior Publication Data
US 2010/0323437 A1 Dec. 23, 2010

(30) Foreign Application Priority Data
Dec. 27, 2006 (JP) .................................. 2006-353390

(51) Int. Cl.
*C12M 1/00* (2006.01)
*A61B 5/00* (2006.01)
*A61B 5/15* (2006.01)

(52) U.S. Cl.
USPC ............ 435/307.1; 422/40; 422/41; 600/573; 600/576; 600/577

(58) Field of Classification Search
USPC .................. 422/40, 41; 435/307.1; 600/573, 600/576, 577
See application file for complete search history.

(56) References Cited

U.S. PATENT DOCUMENTS

| | | | | |
|---|---|---|---|---|
| 4,967,919 A | * | 11/1990 | Earhart | 215/247 |
| 5,027,966 A | * | 7/1991 | Yadock | 220/230 |
| 5,527,513 A | * | 6/1996 | Burns | 422/549 |
| 5,552,117 A | * | 9/1996 | Burns | 422/547 |
| 5,860,937 A | * | 1/1999 | Cohen | 600/576 |

(Continued)

FOREIGN PATENT DOCUMENTS

| | | |
|---|---|---|
| JP | 05-168611 | 7/1993 |
| JP | 06-194280 | 7/1994 |

(Continued)

*Primary Examiner* — Sean Dougherty
(74) *Attorney, Agent, or Firm* — Novak Druce Connolly Bove + Quigg LLP

(57) ABSTRACT

A vacuum blood collection tube (100) comprises a bottomed tube (101) composed of a low temperature resistant material that is less susceptible to low temperature fracture when cryopreserved at ultra-low temperature, a stopper (102) having a needle piercing portion (113) composed of a rubber material that can be pierced with a blood collection needle (110), and a cryopreservation cap (103) composed of the low temperature resistant material. Before blood collection, the stopper (102) is attached to the bottomed tube (101) to maintain the reduced pressure state inside the bottomed tube (101). Thus, blood collection by a vacuum blood collection method is possible. After blood collection, the cryopreservation cap (103) is attached to the bottomed tube (101), so that the liquid tight state of the bottomed tube (101) is maintained, and cryopreservation at ultra-low temperature as it is possible. Thus, the collected blood sample can be cryopreserved at ultra-low temperature as it is, without being transferred to another blood storage container, so that effort and burden on an operator can be significantly reduced.

11 Claims, 27 Drawing Sheets

(56) References Cited

U.S. PATENT DOCUMENTS

| | | | |
|---|---|---|---|
| 6,001,087 A * | 12/1999 | Zurcher | 604/411 |
| 6,497,325 B1 * | 12/2002 | Karg et al. | 210/516 |
| 6,749,078 B2 * | 6/2004 | Iskra | 220/23.87 |
| 7,959,866 B2 * | 6/2011 | Crawford et al. | 422/550 |
| 2002/0104840 A1 * | 8/2002 | Iskra | 220/23.87 |
| 2005/0000962 A1 * | 1/2005 | Crawford et al. | 220/23.87 |
| 2005/0037165 A1 * | 2/2005 | Ahern et al. | 428/35.7 |
| 2005/0065454 A1 * | 3/2005 | Manoussakis | 600/576 |

FOREIGN PATENT DOCUMENTS

| | | |
|---|---|---|
| JP | 3019393 | 10/1995 |
| JP | 08-308816 | 11/1996 |
| JP | 2005-052638 | 3/2005 |
| JP | 2005-253538 | 9/2005 |
| JP | 2005-261965 | 9/2005 |

* cited by examiner

Fig. 9
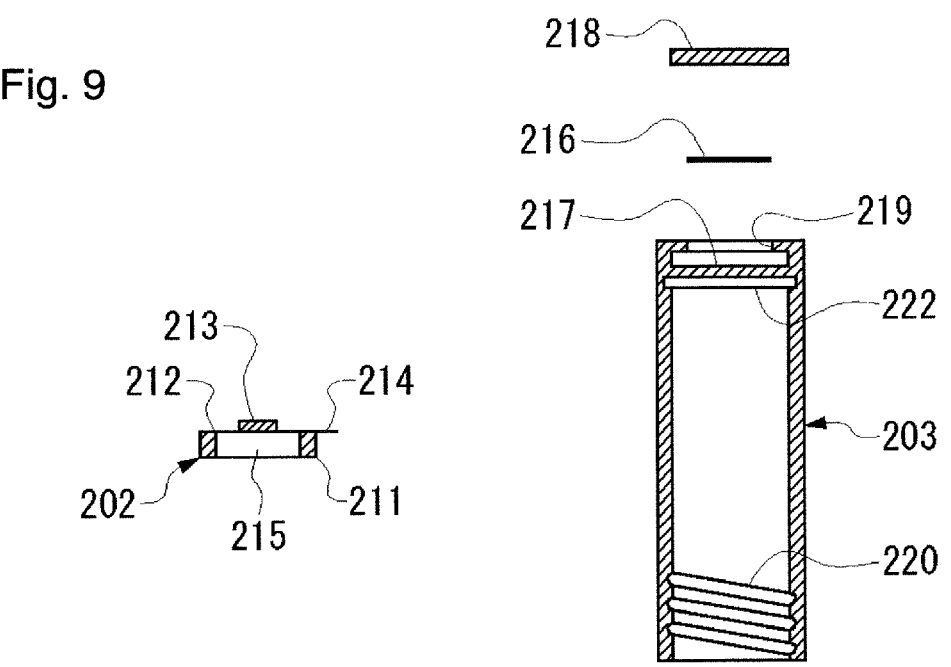
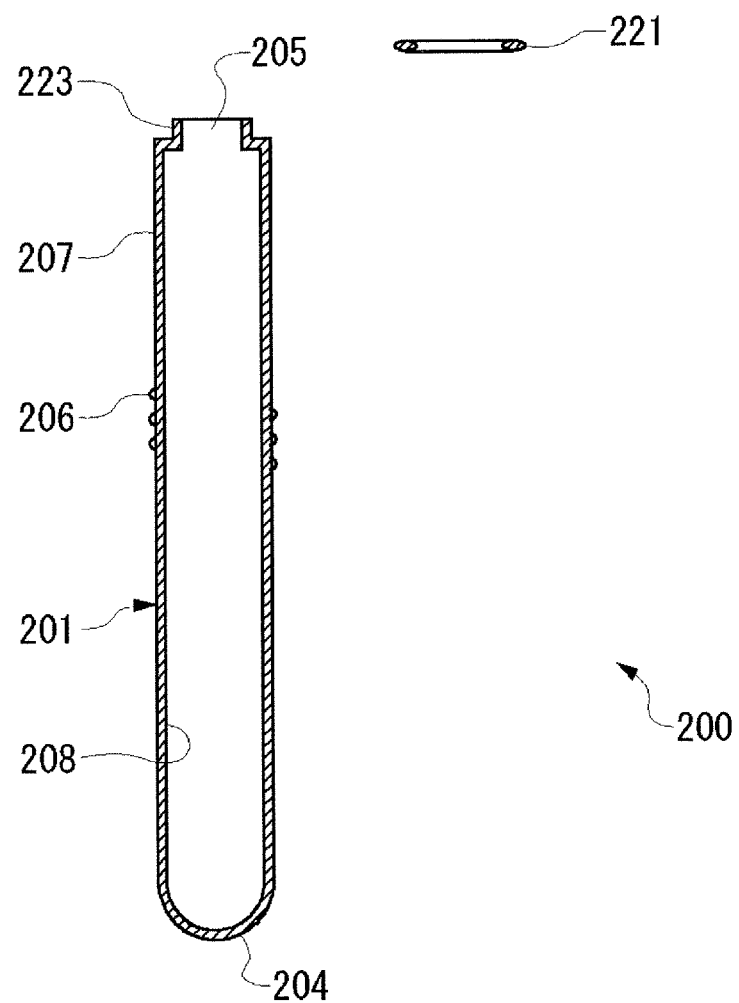

Fig. 23
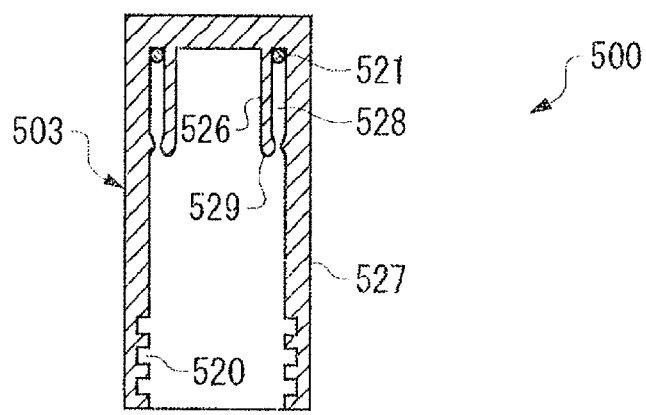
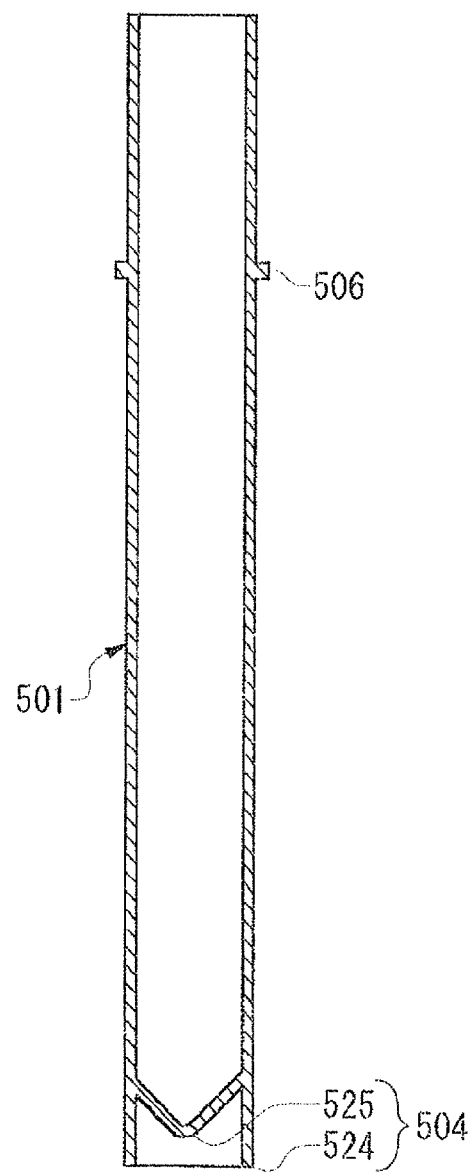

VACUUM BLOOD COLLECTION TUBE

TECHNICAL FIELD

The present invention relates to a vacuum blood collection tube in which a collected blood sample can be cryopreserved as it is.

BACKGROUND

A vacuum blood collection tube is widely used in biochemical tests, blood sugar measurement, erythrocyte sedimentation rate tests, blood coagulation measurement, serological tests, and hematological tests because of its easy operation for blood collection. Conventionally, as the vacuum blood collection tube, one in which a rubber stopper that can be pierced with a blood collection needle is attached to a bottomed tube having an opening has been known. For example, such a vacuum blood collection tube is disclosed in Japanese Patent Laid-Open No. 2005-253538 (pages 6 to 10, FIG. 1) and Japanese Patent Laid-Open No. 2005-261965 (pages 6 to 8, FIG. 1). In a conventional vacuum blood collection tube, before blood collection, the stopper is attached to the opening of the bottomed tube, and the stopper is in close contact with the opening of the bottomed tube, so that the reduced pressure state inside the bottomed tube is maintained. During blood collection, one end of a blood collection needle is inserted into a blood vessel of a subject, and then, the other end of the blood collection needle is pierced into the needle-piercing portion of the stopper. Then, due to the pressure difference between the pressure inside the blood vessel and the pressure inside the bottomed tube, the collection of blood from the subject is performed. Thus, in the conventional vacuum blood collection tube, blood collection can be performed by a vacuum blood collection method. Even after the blood collection needle is pulled out, the rubber stopper is elastically deformed to close the needle hole, so that liquid tightness is kept. Therefore, the collected blood sample (also referred to as a specimen) is prevented from leaking from the needle hole during blood collection.

Generally, in each of the above-described tests using the vacuum blood collection tube, a blood test should be performed as soon as possible after blood collection. In a blood sample collected in the vacuum blood collection tube, the cold activation of complement occurs, so that the blood specimen is quickly subjected to each test rather than being held at low temperature. Therefore, so far, the blood sample collected in the vacuum blood collection tube has not been preserved as whole blood for a long period of several days or more. In other words, so far, the purpose of development has not been to store blood after blood collection, in the vacuum blood collection tube, for a long period.

On the other hand, in recent years, a test for examining the relationship between the genes of a patient and the effect and side effect of various medicines to provide medication and a treatment method suitable for the individual patient (PGx test) has been performed in parallel with clinical research and a clinical trial. In the PGx test, whole blood is generally used for the analysis of DNA diversity, RNA expression, and the like.

In the PGx test, blood cell components themselves of blood are not the objects to be tested, and DNA present in the nucleus of a nucleated cell, such as a white blood cell and a lymphocyte, or RNA (mRNA) made using DNA as a template, and protein biosynthesized based on the RNA information are objects to be tested. Therefore, in the PGx test, unlike the above-described biochemical test, it is required that whole blood is frozen and stored at ultra-low temperature to prevent the decomposition of DNA, RNA, and protein. Also, when a blood sample once frozen is thawed again, DNA damage occurs, and DNA extraction efficiency decreases. Therefore, it is required that after a blood sample is frozen in a blood collection facility, the blood sample is stored at ultra-low temperature for a long period so as not to thaw again.

However, in the conventional vacuum blood collection tube, a plastic material, such as PET, is often used, as the material of the vacuum blood collection tube, and a material that can endure storage at ultra-low temperature is not used. Therefore, when it is attempted to cryopreserve the conventional vacuum blood collection tube as it is, low temperature fracture may occur when the conventional vacuum blood collection tube is immersed in liquid nitrogen. Also, in the conventional vacuum blood collection tube, a metal lid or a plastic lid is used to bring the stopper into close contact with the bottomed tube. But, different materials are often used for the bottomed tube, the stopper, and the lid, and when these are held at ultra-low temperature, a clearance may be produced between the stopper or the lid and the bottomed tube due to difference in the degree of thermal shrinkage. In such a case, from the clearance, external liquid nitrogen and the like may enter the vacuum blood collection tube, and the sample inside the vacuum blood collection tube may leak to the outside.

Therefore, when a whole blood specimen is stored, it is necessary to separately prepare a blood storage container for cryopreservation that can endure preservation at ultra-low temperature, and, after collecting blood in the vacuum blood collection tube, transfer the blood sample to the blood storage container. In this blood storage container, no clearance is produced even at ultra-low temperature, so that liquid tightness is kept. In other words, there is no possibility that from the clearance, external liquid nitrogen and the like enter the vacuum blood collection tube, and the sample inside the vacuum blood collection tube leaks to the outside. However, the operation of transferring the blood sample from the vacuum blood collection tube to the blood storage container not only requires labor for the operation itself, but also may cause the blood spilled or scattered during the operation. Therefore, effort and burden on the operator of the transferring operation are very large.

SUMMARY OF DISCLOSURE OF THE INVENTION

Problems to be Solved by the Invention

The present invention has been made in view of the above background. It is an object of the present invention to provide a vacuum blood collection tube in which a collected blood sample can be cryopreserved at ultra-low temperature as it is, without transferring the blood to another container, after blood collection.

Means for Solving the Problems

One aspect of the present invention is a vacuum blood collection tube. This vacuum blood collection tube comprises a bottomed tube composed of a low temperature resistant material that is less susceptible to low temperature fracture when cryopreserved at an ultra-low temperature of −40° C. to −200° C., and having a bottom portion at one end and an opening at the other end; a stopper attached to the opening of the bottomed tube before blood collection, being in close contact with the opening of the bottomed tube so that the reduced pressure state inside the bottomed tube can be maintained, and having a needle piercing portion composed of a rubber material that can be pierced with a blood collection needle; and a cryopreservation cap composed of the low temperature resistant material, attached to the opening of the bottomed tube after blood collection, and sealing the opening of the bottomed tube under the condition of the ultra-low temperature so that the liquid tight state of the bottomed tube can be maintained.

Another aspect of the present invention is a method of manufacturing the above vacuum blood collection tube. This method of manufacturing the vacuum blood collection tube comprises preparing a first mold having the shape of the outer periphery of the cryopreservation cap on an inner surface, and a second mold having the shape of the inner periphery of the cryopreservation cap on an outer surface; closing the first mold and the second mold to form a cavity having the shape of the cryopreservation cap; heating and melting a low temperature resistant material that is less susceptible to low temperature fracture when cryopreserved at an ultra-low temperature of −40° C. to −200° C. to inject the low temperature resistant material into the cavity; and cooling and solidifying the low temperature resistant material, and then, when opening the first mold and the second mold to remove the cryopreservation cap, pulling out the second mold, while rotating the second mold, to form a thread groove portion on the inner peripheral surface of the cryopreservation cap.

The present invention includes other aspects as described below. Therefore, the disclosure of this invention is intended to provide part of the aspects of the present invention and is not intended to limit the scope of the invention described and claimed herein.

BRIEF DESCRIPTION OF THE DRAWINGS

FIG. 9 is a cross-sectional view of the vacuum blood collection tube (the bottomed tube, the stopper, and the cryopreservation cap);

FIG. 23 is a plan view of a vacuum blood collection tube (a bottomed tube and a cryopreservation cap) in a fifth embodiment;

Figure 1:
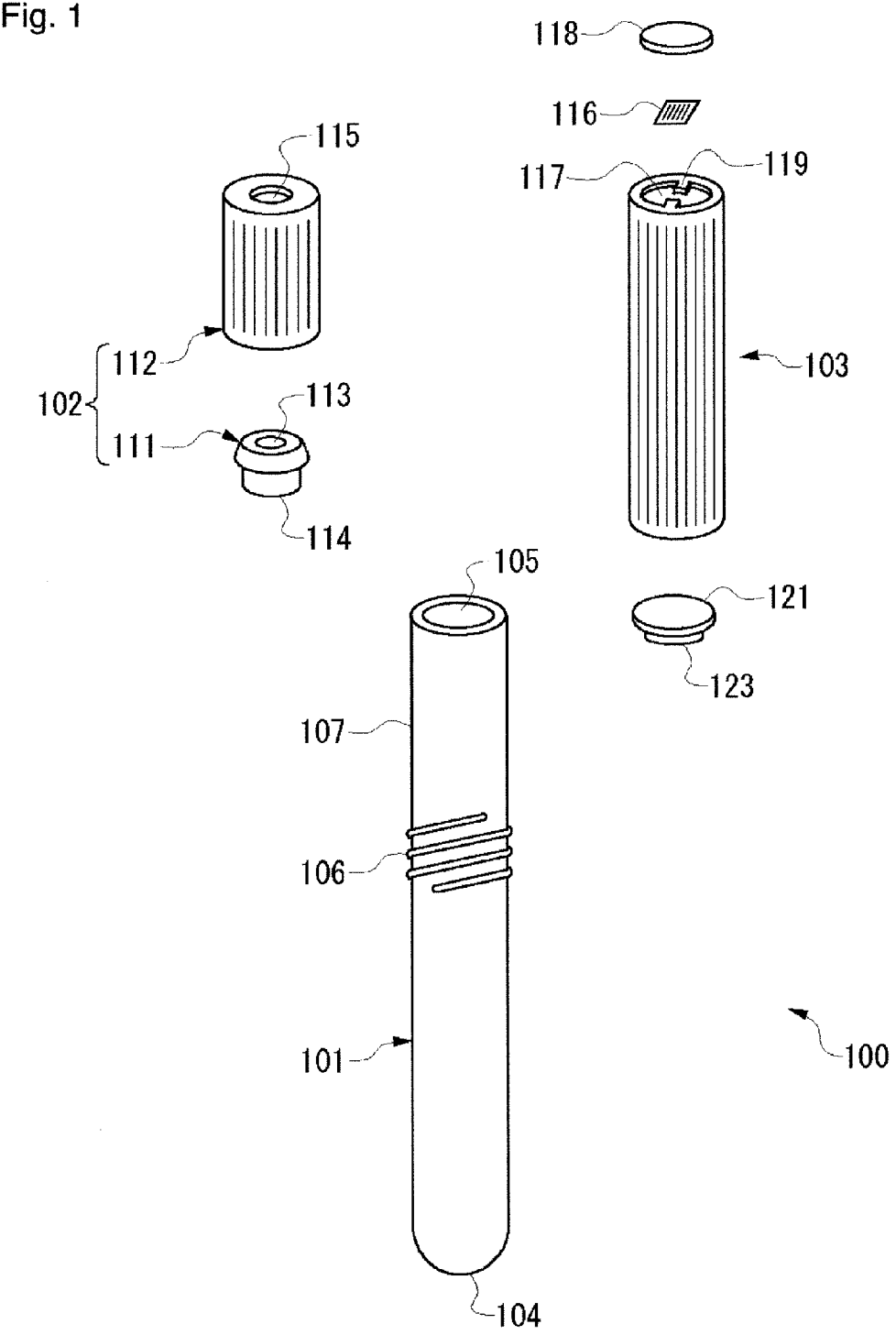
FIG. 1 is a perspective view of a vacuum blood collection tube (a bottomed tube, a stopper, and a cryopreservation cap) in a first embodiment.

DESCRIPTION OF SYMBOLS 100 vacuum blood collection tube
101 bottomed tube
102 stopper
103 cryopreservation cap
104 bottom portion
105 opening
106 thread portion (tube side thread portion)
107 thread absent portion
108 thin film
109 blood coagulation preventing agent
110 blood collection needle
111 needle piercing member
112 cap member
113 needle piercing portion
116 bar code (identification mark)
117 attachment portion
118 cover
120 thread groove portion (cap side thread portion)

BEST MODE FOR CARRYING OUT THE INVENTION

The detailed description of the present invention will be described below. However, the following detailed description and the accompanying drawings do not limit the invention. Instead, the scope of the invention is defined by the appended claims.

The vacuum blood collection tube of the present invention comprises a bottomed tube composed of a low temperature resistant material that is less susceptible to low temperature fracture when cryopreserved at an ultra-low temperature of −40° C. to −200° C., and having a bottom portion at one end and an opening at the other end; a stopper attached to the opening of the bottomed tube before blood collection, being in close contact with the opening of the bottomed tube so that the reduced pressure state inside the bottomed tube can be maintained, and having a needle piercing portion composed of a rubber material that can be pierced with a blood collection needle; and a cryopreservation cap composed of the low temperature resistant material, attached to the opening of the bottomed tube after blood collection, and sealing the opening of the bottomed tube under the condition of the ultra-low temperature so that the liquid tight state of the bottomed tube can be maintained.

Thus, before blood collection, the stopper is attached to the opening of the bottomed tube, and the stopper is in close contact with the opening of the bottomed tube, so that the reduced pressure state inside the bottomed tube is maintained. During blood collection, one end of the blood collection needle is inserted into a blood vessel of a subject, and then, the other end of the blood collection needle is pierced into the needle-piercing portion of the stopper. Then, due to the pressure difference between the pressure inside the blood vessel and the pressure inside the bottomed tube, the collection of blood from the subject is performed. Thus, blood collection can be performed by a vacuum blood collection method.

After blood collection, the cryopreservation cap is attached to the opening of the bottomed tube, and the opening of the bottomed tube is sealed, so that the liquid tight state of the bottomed tube is maintained. In this case, the bottomed tube and the cryopreservation cap are composed of the low temperature resistant material that is less susceptible to low temperature fracture when cryopreserved at ultra-low temperature. Thus, the vacuum blood collection tube having the cryopreservation cap attached has the function of a blood storage container for cryopreservation at ultra-low temperature. Therefore, a blood storage container for cryopreservation that can endure preservation at ultra-low temperature need not be separately prepared. Also, the collected blood sample can be cryopreserved at ultra-low temperature as it is, without being transferred to another blood storage container. Thus, effort and burden on an operator are significantly reduced.

Also, in the vacuum blood collection tube of the present invention, the cryopreservation cap may be attached to the opening of the bottomed tube, in exchange of the stopper, after blood collection.

In this case, after blood collection, the stopper is removed from the opening of the bottomed tube, and the cryopreservation cap is attached to the opening of the bottomed tube, in exchange of the stopper. Thus, the opening of the bottomed tube is sealed, so that the liquid tight state of the bottomed tube is maintained. Thus, the vacuum blood collection tube having the cryopreservation cap attached has the function of a blood storage container for cryopreservation at ultra-low temperature.

Also, in the vacuum blood collection tube of the present invention, the cryopreservation cap may be attached to the opening of the bottomed tube, covering the stopper, after blood collection.

In this case, after blood collection, the cryopreservation cap is attached to the opening of the bottomed tube, covering the stopper, without removing the stopper from the opening of the bottomed tube. Thus, the opening of the bottomed tube is sealed, so that the liquid tight state of the bottomed tube is maintained. Thus, the vacuum blood collection tube having the cryopreservation cap attached has the function of a blood storage container for cryopreservation at ultra-low temperature.

Also, in the vacuum blood collection tube of the present invention, the stopper may comprise a needle piercing member attached to the opening of the bottomed tube before blood collection and composed of a rubber material that can be pierced with a blood collection needle, and a cap member attached to the opening of the bottomed tube over the needle piercing member before blood collection and bringing the needle piercing member into close contact with the bottomed tube so that the reduced pressure state inside the bottomed tube can be maintained.

Thus, the stopper of the vacuum blood collection tube is composed of two members, the needle piercing member and the cap member. Therefore, compared with a case where the stopper is composed of one member, the stopper can be manufactured relatively easily even if the configuration of the needle piercing member and the cap member is complicated.

Also, in the vacuum blood collection tube of the present invention, a tube side thread portion may be provided on a surface of the bottomed tube, and a cap side thread portion threadedly engaged with the tube side thread portion may be provided on a surface of the cryopreservation cap. The cryopreservation cap may be threadedly attached to the bottomed tube after blood collection.

Thus, when the cryopreservation cap is attached to the opening of the bottomed tube after blood collection, the tube side thread portion of the bottomed tube and the cap side thread portion of the cold preservation cap are threadedly engaged with each other. Thus, by threadedly attaching the cryopreservation cap to the bottomed tube, the opening of the bottomed tube is tightly sealed, so that the liquid tightness of the bottomed tube can be enhanced.

Also, in the vacuum blood collection tube of the present invention, the tube side thread portion and the cap side thread portion may be multiple threads.

Thus, the tube side thread portion and the cap side thread portion are in contact with each other at a plurality of places, and force is equally applied to both. Therefore, the cryopreservation cap can be tightly threadedly attached to the bottomed tube, so that the liquid tightness of the bottomed tube is improved. Also, in the multiple thread, the lead is a plurality of times the pitch, so that the amount of rotation when threadedly attaching the cryopreservation cap to the bottomed tube is only small, therefore, the tightening operation is easy, and the operability is improved.

Also, in the vacuum blood collection tube of the present invention, the tube side thread portion may be a thread portion provided on the outer peripheral surface of the bottomed tube, and the cap side thread portion may be a thread groove portion provided on the inner peripheral surface of the cryopreservation cap.

Thus, when the cryopreservation cap is attached to the opening of the bottomed tube after blood collection, the thread groove portion on the inner peripheral surface of the cold preservation cap is threadedly engaged with the thread portion on the outer peripheral surface of the bottomed tube. Thus, by threadedly attaching the cryopreservation cap to the bottomed tube, the opening of the bottomed tube is tightly sealed, so that the liquid tightness of the bottomed tube can be enhanced.

Also, in the vacuum blood collection tube of the present invention, a thread absent portion in which the thread portion is not present may be provided on the outer peripheral surface of the bottomed tube at a position on the opening side from the thread portion, and the stopper may be attached to the thread absent portion.

Thus, the stopper of the vacuum blood collection tube is attached to the thread absent portion on the outer peripheral surface of the bottomed tube. Therefore, the thread portion of the bottomed tube is prevented from becoming an obstacle when the stopper is attached to the opening of the bottomed tube. Therefore, the stopper can be smoothly attached to the bottomed tube.

Also, in the vacuum blood collection tube of the present invention, the cryopreservation cap may comprise an attachment portion to which an identification mark for identifying a collected blood sample is attached.

Thus, the identification mark is attached to the attachment portion of the cryopreservation cap. By using this identification mark, the collected blood sample can be easily identified.

Also, in the vacuum blood collection tube of the present invention, a thin film having a gas barrier property may be formed on the inner peripheral surface of the bottomed tube.

Thus, the thin film having a gas barrier property is formed on the inner peripheral surface of the bottomed tube, so that the air tightness of the bottomed tube is improved. Therefore, the reduced pressure state inside the bottomed tube can be maintained for a long period.

Also, in the vacuum blood collection tube of the present invention, a blood coagulation preventing agent for preventing the coagulation of collected blood may be placed in the bottomed tube.

Thus, the blood coagulation preventing agent is placed in the bottomed tube, so that when blood is collected using the vacuum blood collection tube, the collected blood immediately comes into contact with the blood coagulation preventing agent. Therefore, the blood coagulation preventing agent immediately acts on the collected blood sample, so that the coagulation of the blood sample can be prevented.

According to the vacuum blood collection tube of the present invention, the collected blood sample can be cryopreserved at ultra-low temperature as it is, without being transferred to another blood storage container, so that effort and burden on the operator can be significantly reduced.

Also, in the vacuum blood collection tube of the present invention, the bottomed tube to which the stopper is attached, and the cryopreservation cap constitute a vacuum blood collection tube set, and the vacuum blood collection tube may comprises a connection part connecting the bottomed tube and the cryopreservation cap.

Thus, the bottomed tube and the cryopreservation cap are connected, so that when a blood sample is collected, the trouble of looking for the cryopreservation cap at the site of the operation of blood collection can be saved.

Also, in the vacuum blood collection tube of the present invention, a set identification mark for identifying the vacuum blood collection tube set may be applied to the bottomed tube and the cryopreservation cap.

Thus, a common set identification mark (for example, a bar code) is applied to both of the bottomed tube and the cryopreservation cap, so that the collected sample can be easily managed.

Also, in the vacuum blood collection tube of the present invention, the low temperature resistant material may be a cyclic olefin copolymer.

This cyclic olefin copolymer has high heat resistance and excellent dimensional stability, can endure the steps of the collection of a blood sample to cryopreservation at ultra-low temperature, and is suitable as the low temperature resistant material of the present invention.

Also, in the vacuum blood collection tube of the present invention, the bottomed tube may comprise a scale for measuring the amount of a collected sample.

Thus, the amount of the collected blood sample can be easily measured.

Also, in the vacuum blood collection tube of the present invention, the bottomed tube may comprise an affixing guide portion showing an affixing reference line for a sample identification mark seal for identifying a collected sample.

Thus, using the affixing guide portion as a reference, the sample identification mark seal (for example, a bar code seal) can be easily affixed along the predetermined affixing direction (for example, the axial direction of the bottomed tube).

Also, in the vacuum blood collection tube of the present invention, the bottom portion of the bottomed tube may have a free-standing bottom part supporting the bottomed tube, to which the cryopreservation cap is attached, so that the bottomed tube can be free-standing, and a concave bottom part having a central portion formed in a concave shape.

The bottomed tube can be temporarily placed vertically using this free-standing bottom part, so that the trouble of using a stand for placing the bottomed tube vertically is eliminated, and the operability is improved. Also, the sample is accumulated in the concave bottom part, so that even if the amount of the sample decreases, the remaining sample can be easily removed by a syringe or the like, and the operability is improved. The concave shape includes, for example, an inverted conical shape, an inverted pyramidal shape, an inverted hemispherical shape (dome shape), and the like.

Also, in the vacuum blood collection tube of the present invention, an annular housing portion having a clearance, into which the other end of the bottomed tube is inserted when the cryopreservation cap is attached to the bottomed tube, is provided in the cryopreservation cap, and a pinch portion in which the width of the clearance is smaller than the thickness of the bottomed tube may be annularly provided in the annular housing portion.

Thus, when the cryopreservation cap is attached to the bottomed tube, the other end of the bottomed tube is pinched in the pinch portion of the annular housing portion, so that the liquid tight state of the bottomed tube can be maintained.

The method of manufacturing a vacuum blood collection tube according to the present invention is a method of manufacturing the above vacuum blood collection tube, comprising preparing a first mold having the shape of the outer periphery of the cryopreservation cap on an inner surface, and a second mold having the shape of the inner periphery of the cryopreservation cap on an outer surface; closing the first mold and the second mold to form a cavity having the shape of the cryopreservation cap; heating and melting a low temperature resistant material that is less susceptible to low temperature fracture when cryopreserved at an ultra-low temperature of −40° C. to −200° C. to inject the low temperature resistant material into the cavity; and cooling and solidifying the low temperature resistant material, and then, when opening the first mold and the second mold to remove the cryopreservation cap, pulling out the second mold, while rotating the second mold, to form a thread groove portion on the inner peripheral surface of the cryopreservation cap.

According to this method, the cryopreservation cap can be manufactured in one step by molding, so that the manufacture of the vacuum blood collection tube becomes easy.

Vacuum blood collection tubes in the embodiments of the present invention will be described below using the drawings. In these embodiments, the cases of vacuum blood collection tubes for cryopreserving blood for a long period for DNA analysis or the like are illustrated. Blood cryopreserved in this manner is used not only for the analysis and research of a drug and reaction to the drug (PGx research) in the development of a medicine, but also as a reference for DNA analysis, for example, for the identification of a suspect in crime investigation, and the identification of a soldier (Self-Defense Force member).

First Embodiment

Figure 2:
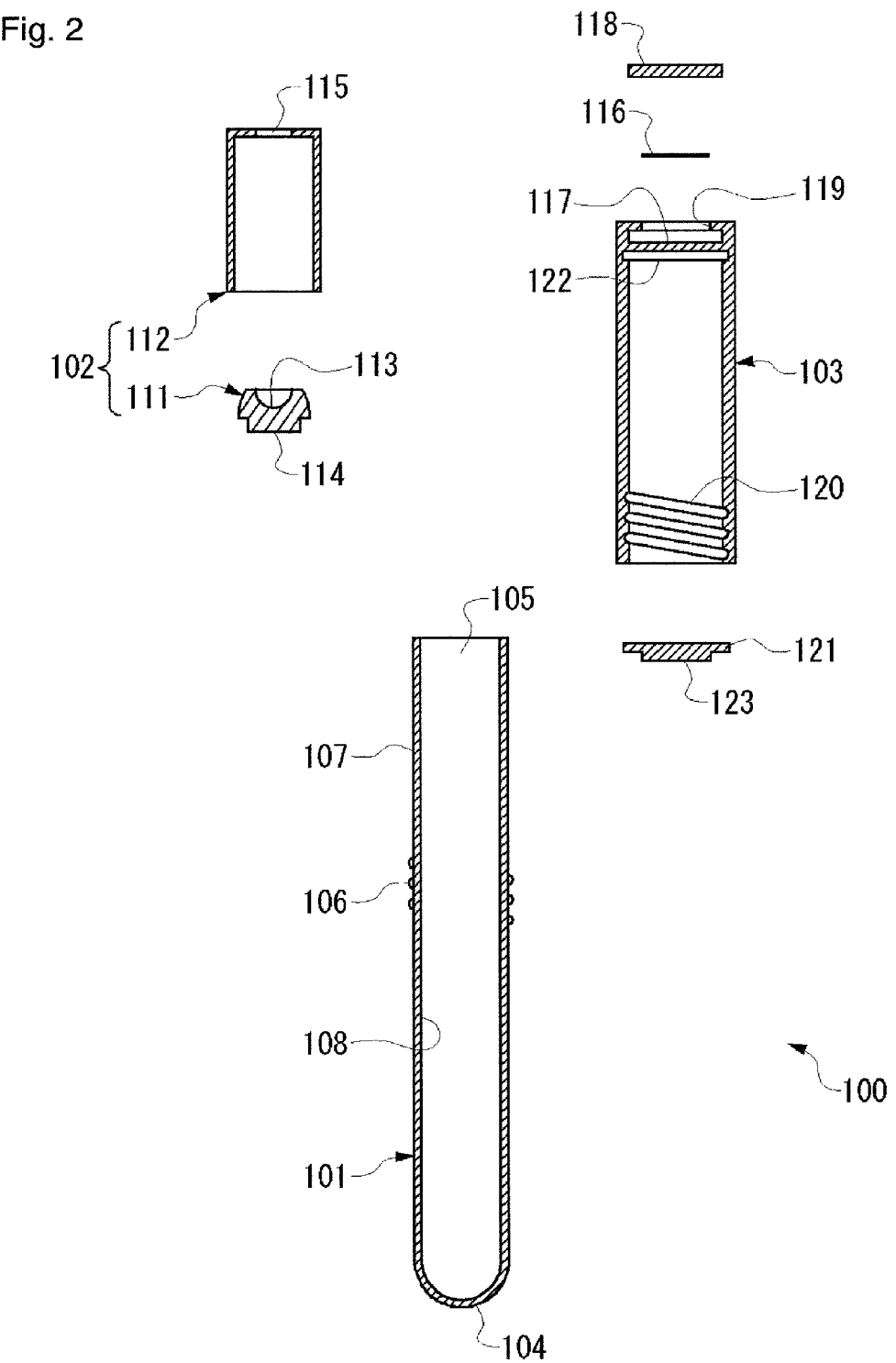
FIG. 2 is a cross-sectional view of the vacuum blood collection tube (the bottomed tube, the stopper, and the cryopreservation cap)

A vacuum blood collection tube in the first embodiment of the present invention is shown in FIG. 1 to FIG. 7. FIG. 1 is a perspective view showing the configuration of the vacuum blood collection tube, and FIG. 2 is a cross-sectional view showing the configuration of the vacuum blood collection tube. As shown in FIG. 1 and FIG. 2, a vacuum blood collection tube 100 comprises a bottomed tube 101, a stopper 102, and a cryopreservation cap 103. In the vacuum blood collection tube 100 in this embodiment, the cryopreservation cap 103 is attached to the bottomed tube 101, in exchange of the stopper 102.

The bottomed tube 101 is generally cylindrical and has a bottom portion 104 at one end and an opening 105 at the other end. A thread portion 106 is provided on the outer peripheral surface of the bottomed tube 101. This thread portion 106 is provided on the surface of the bottomed tube 101 and corresponds to the tube side thread portion of the present invention.

The above thread portion 106 is not provided on the outer peripheral surface of the bottomed tube 101 at a position near the opening 105. In other words, it can also be said that a thread absent portion 107 in which the thread portion 106 is not present is provided on the outer peripheral surface of the bottomed tube 101 at a position on the opening 105 side from the thread portion 106. The stopper 102 is attached to this thread absent portion 107 (see FIG. 3 and FIG. 4). Therefore, it can also be said that the thread portion 106 of the bottomed tube 101 is provided at a non-interfering position where the thread portion 106 does not become an obstacle when the stopper 102 is mounted on the bottomed tube 101.

The bottomed tube 101 is composed of a low temperature resistant material. This low temperature resistant material refers to a material that is less susceptible to low temperature fracture when cryopreserved at an ultra-low temperature of $-40°$ C. to $-200°$ C. In other words, it can be said that the low temperature resistant material is a material suitable for storage at ultra-low temperature. In this embodiment, for example, polycarbonate (PC), polypropylene (PP), and the like are used as this low temperature resistant material.

Here, the ultra-low temperature refers to a temperature of $-40°$ C. to $-200°$ C. In this case, a collected blood sample is often cryopreserved at $-40°$ C. or less, so that the low temperature resistant material is desirably a material that is less susceptible to low temperature fracture when cryopreserved at $-40°$ C. or less. Usually, the collected blood sample is often cryopreserved at $60°$ C. or less, so that the low temperature resistant material is more desirably a material that is less susceptible to low temperature fracture when cryopreserved at $-60°$ C. or less. Particularly, the collected blood sample is often cryopreserved at about $-80°$ C., so that the low temperature resistant material is more desirably a material that is less susceptible to low temperature fracture when cryopreserved at $-80°$ C. or less. Also, the collected blood sample can be cryopreserved using liquid nitrogen (boiling point: $-196°$ C.), so that the low temperature resistant material is desirably a material that is less susceptible to low temperature fracture when cryopreserved at $-200°$ C.

In this embodiment, as the low temperature resistant material, a cyclic olefin copolymer is used. One example of the cyclic olefin copolymer includes TOPAS (registered trademark) obtained by copolymerizing norbornene and ethylene using a metallocene catalyst, or the like. Such a cyclic olefin copolymer has optical properties comparable to those of PMMA (polymethylmethacrylate, an acrylic resin), higher heat resistance than PC (a polycarbonate resin), and dimensional stability superior to that of PMMA and PC, can endure the steps of the collection of a blood sample to cryopreservation at ultra-low temperature, and is suitable as the low temperature resistant material.

Here, the present invention is described assuming cryopreservation at an ultra-low temperature of $-40°$ C. to $-200°$ C., but it is needless to say that the vacuum blood collection tube 100 of the present invention may be used for cryopreservation at a temperature higher than this (for example, $-20°$ C.).

A thin film 108 having a gas barrier property is formed on the inner peripheral surface of the bottomed tube 101. Also, in this case, other than forming the thin film 108 having a gas barrier property on the inner peripheral surface of the bottomed tube 101, the bottomed tube 101 itself may be manufactured using a material having a gas barrier property. Here, the gas barrier property refers to the property of blocking so that gas does not leak to the outside, that is, the property of keeping internal airtightness. In this embodiment, as a material having a high gas barrier property, for example, a compound of a polyethylene terephthalate copolymer and a polyethylene naphthalate copolymer, a copolymerized polyester resin containing terephthalic acid and isophthalic acid as acid components and ethylene glycol as a diol component and having crystallinity, and the like are used. Also, a thin film layer of ceramic may be formed on the surface (inner peripheral surface and/or outer peripheral surface) of the bottomed tube 101 of an ethylene-polypropylene random copolymer by a plasma chemical vapor deposition (CVD) method. Further, the inner surface of the bottomed tube 101 made of plastic may be coated with a thin film of silicon oxide containing a carbon atom.

Figure 3:
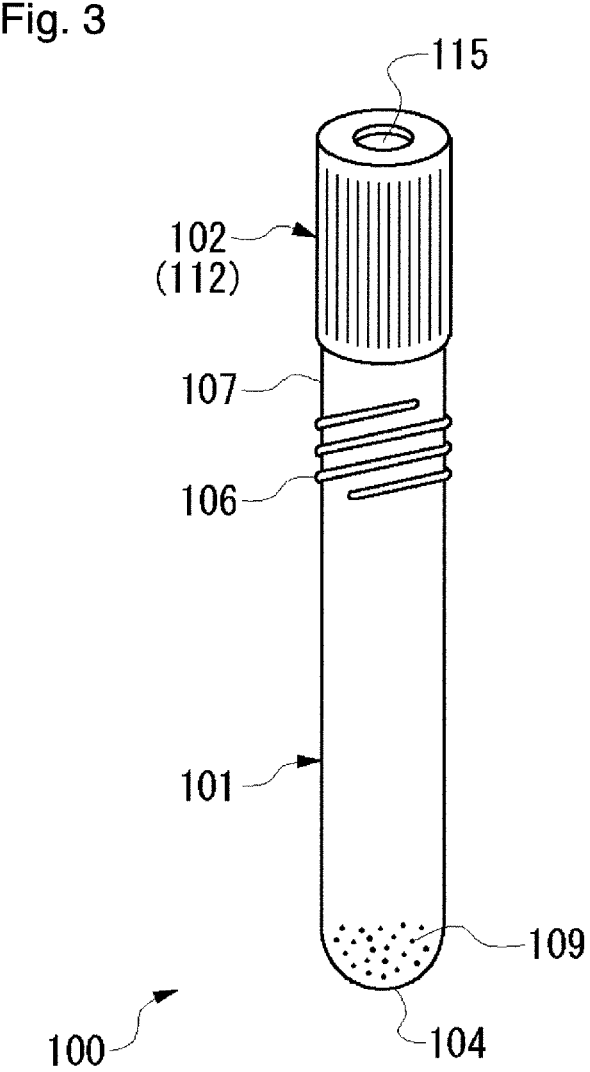
FIG. 3 is a perspective view of the vacuum blood collection tube before blood collection.

Also, a blood coagulation preventing agent 109 for preventing the coagulation of a collected blood is placed in the bottomed tube 101 (see FIG. 3). In this embodiment, as the blood coagulation preventing agent 109, for example, EDTA-2Na, EDTA-2K, heparin, sodium citrate, and the like are used. Also, in addition, as the blood coagulation preventing agent 109, for example, sodium fluoride, ACD (acid citrate dextrose solution), and the like may be used. In this case, a backflow prevention mechanism may be provided in a blood collection needle 110. Thus, the backflow of blood can be prevented during blood collection, and the blood coagulation preventing agent 109 dissolved in blood can be prevented from flowing back with the blood to the subject.

Figure 4:
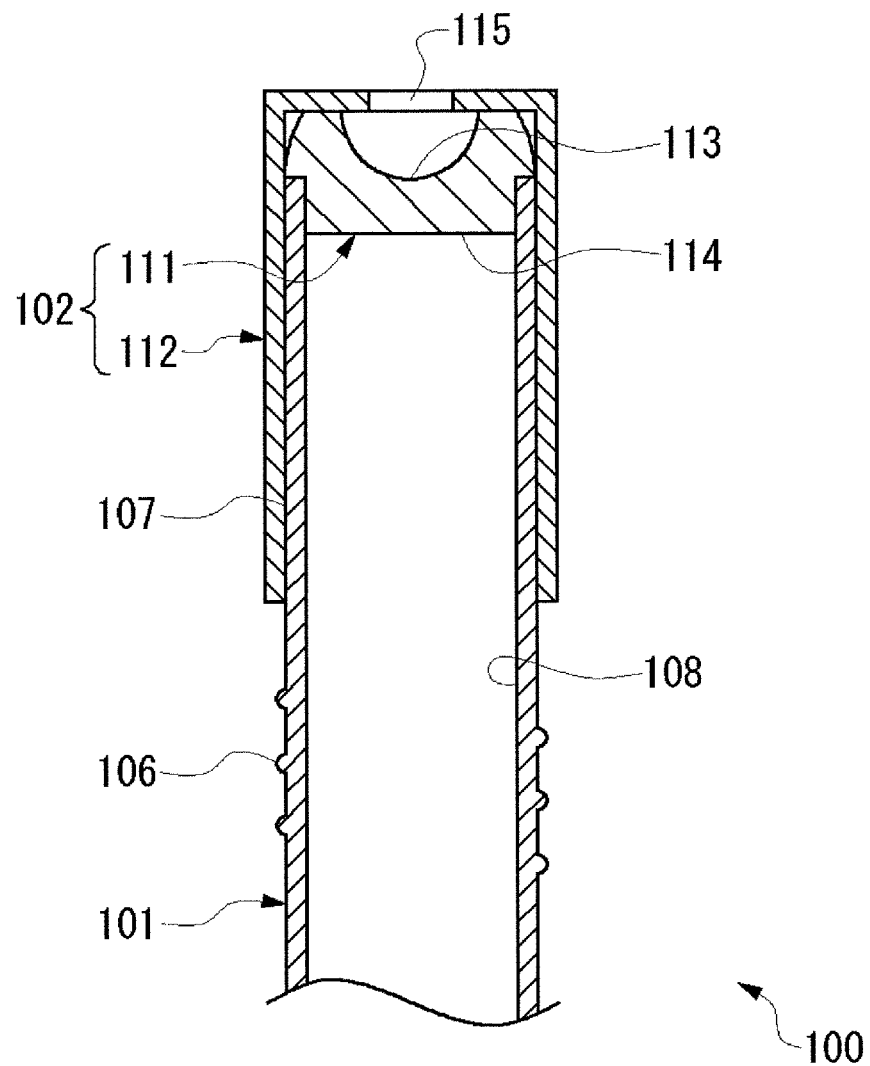
FIG. 4 is an enlarged cross-sectional view of the vacuum blood collection tube before blood collection.
Figure 5:
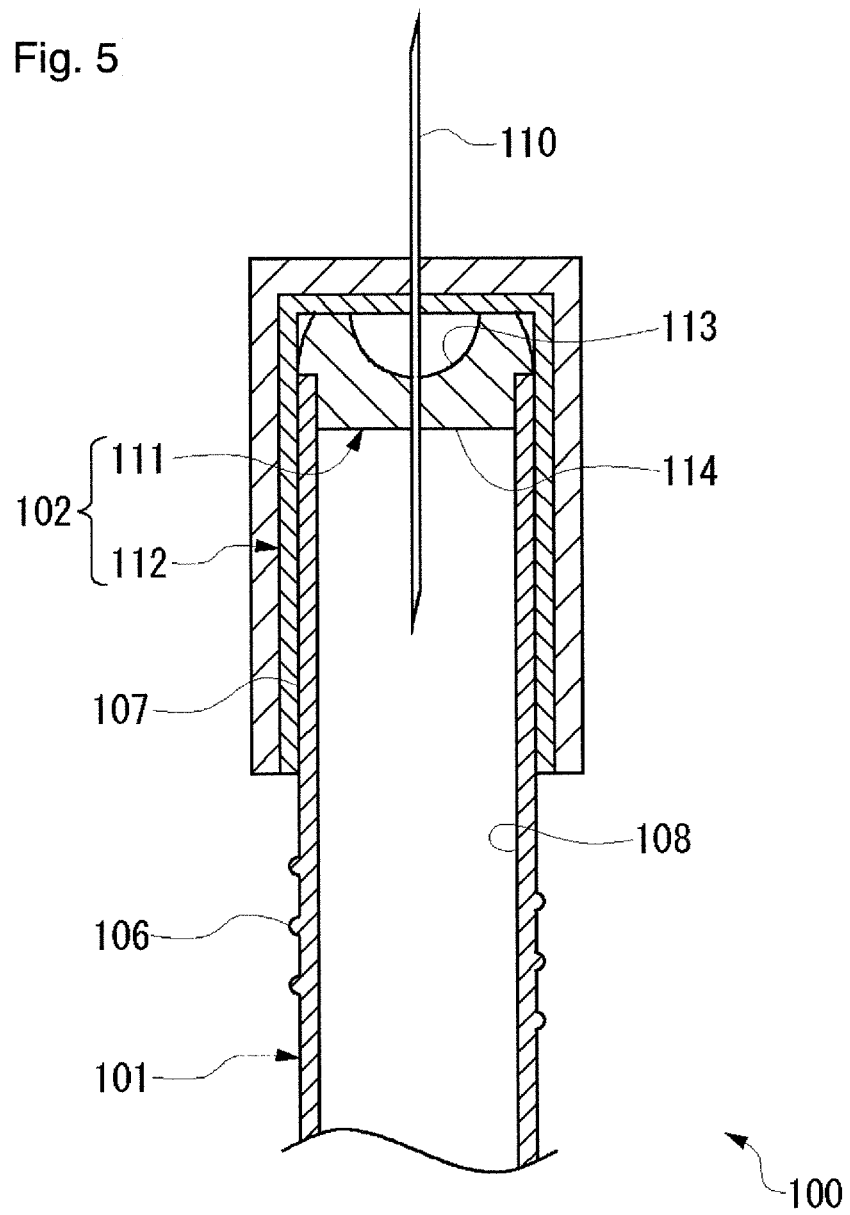
FIG. 5 is an enlarged cross-sectional view of the vacuum blood collection tube during blood collection.

FIG. 3 is a perspective view of the vacuum blood collection tube 100 before blood collection, and FIG. 4 is a cross-sectional view of the vacuum blood collection tube 100 before blood collection. FIG. 5 is a cross-sectional view schematically showing the vacuum blood collection tube 100 during blood collection. As shown in FIG. 3 and FIG. 4, the stopper 102 is attached to the opening 105 of the bottomed tube 101 before blood collection. This stopper 102 is used during blood collection and can also be said to be the stopper 102 for blood collection.

The stopper 102 is composed of a needle piercing member 111 and a cap member 112 (see FIG. 1). A needle piercing portion 113 that is pierced with the blood collection needle 110 is concavely provided in the central portion of the upper surface of the needle piercing member 111. The needle piercing member 111 has an outer diameter generally equal to the outer diameter of the opening 105 of the bottomed tube 101. Also, a stopper convex portion 114 having an outer diameter generally equal to the inner diameter of the opening 105 of the bottomed tube 101 is provided in the lower portion of the needle piercing member 111.

This needle piercing member 111 is composed of a rubber material that can be pierced with the blood collection needle 110. In this embodiment, as the rubber material, for example, synthetic rubbers, such as a butyl rubber and a halogenated butyl rubber, a silicone rubber, elastomers, such as a PP/vulcanized EPDM type (Sarlink), are used. The needle piercing member 111 composed of such a rubber material closes a needle hole due to elastic deformation, even after the blood collection needle 110 is pulled out, so that liquid tightness can be kept.

The cap member 112 is generally cylindrical, and a needle insertion hole 115 through which the blood collection needle 110 is inserted is provided in the upper surface of the cap member 112 (see FIG. 1). The needle insertion hole 115 of this cap member 112 is provided at a position corresponding to the needle piercing portion 113 of the needle piercing member 111. In this embodiment, the needle insertion hole 115 is provided in the central portion of the upper surface of the cap member 112.

As shown in FIG. 3 and FIG. 4, the needle piercing member 111 is attached to the opening 105 of the bottomed tube 101, and the cap member 112 is attached over the needle piercing member 111. Thus, the needle piercing member 111 is brought into close contact with the bottomed tube 101, so that the airtightness inside the bottomed tube 101 can be kept.

In the vacuum blood collection tube 100 before blood collection, the pressure is reduced inside the bottomed tube 101. In this case, the needle piercing member 111 is brought into close contact with the bottomed tube 101 by the cap member 112, so that airtightness is kept, therefore, due to the pressure difference between the air pressure inside the bottomed tube 101 and atmospheric pressure, the stopper 102 is pressed against the bottomed tube 101. Thus, the reduced pressure state inside the bottomed tube 101 before blood collection is maintained.

Figure 6:
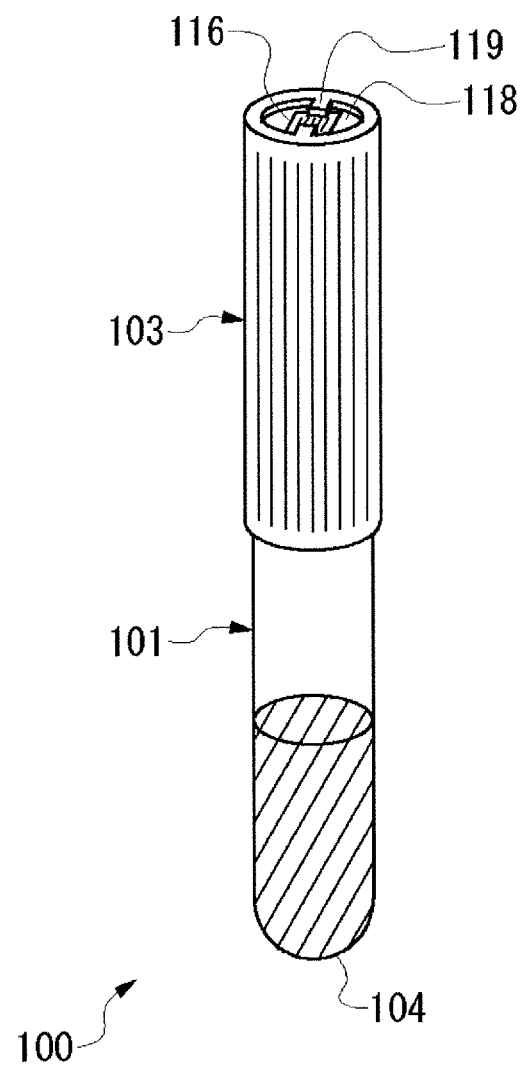
FIG. 6 is a perspective view of the vacuum blood collection tube after blood collection (during cryopreservation)
Figure 7:
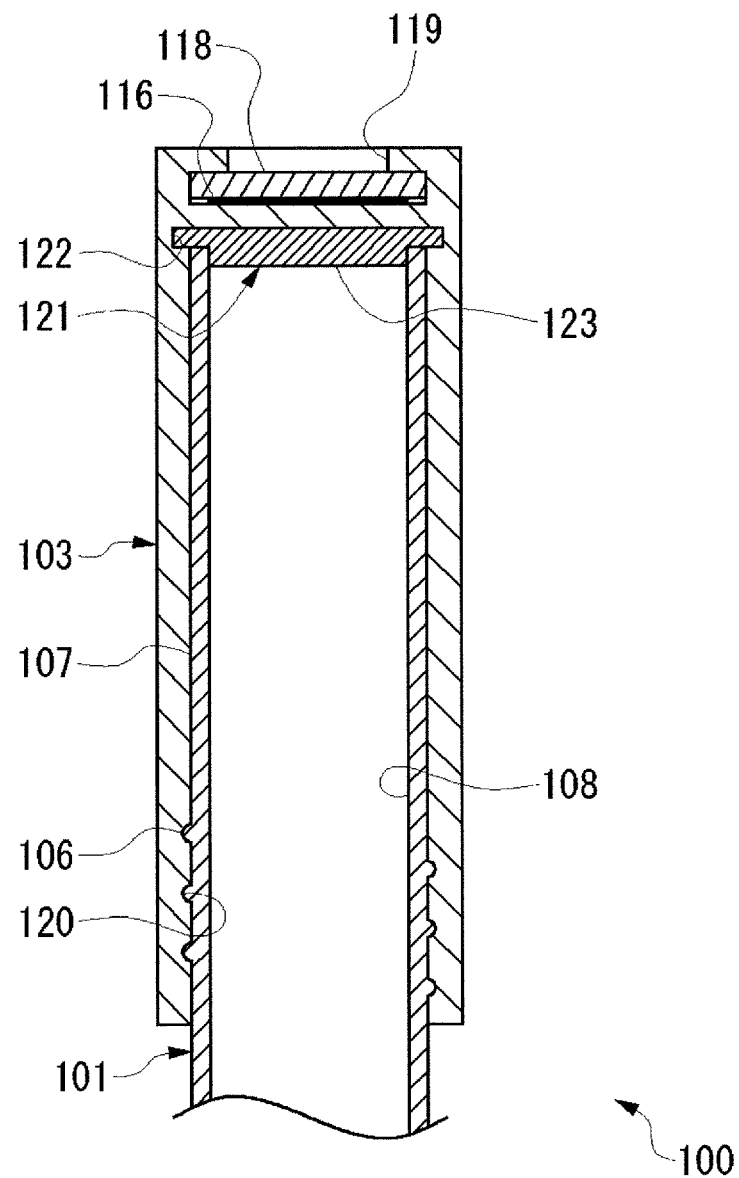
FIG. 7 is an enlarged cross-sectional view of the vacuum blood collection tube after blood collection (during cryopreservation)

FIG. 6 is a perspective view of the vacuum blood collection tube 100 at the time of cryopreservation after blood collection, and FIG. 7 is a cross-sectional view of the vacuum blood collection tube 100 at the time of cryopreservation after blood collection. As shown in FIG. 6 and FIG. 7, the cryopreservation cap 103 is attached to the opening 105 of the bottomed tube 101 when the collected blood is cryopreserved. In this embodiment, the cryopreservation cap 103 is attached to the opening 105 of the bottomed tube 101, in exchange of the stopper 102, after blood collection.

The cryopreservation cap 103 is generally cylindrical, and an attachment portion 117 to which a bar code 116 is attached is concavely provided on the upper surface of the cryopreservation cap 103 (see FIG. 1). A cover 118 covering the bar code 116 is attached to the attachment portion 117. Also, a pair of projecting press pieces 119 for pressing the attached cover 118 is provided in the attachment portion 117. These projecting press pieces 119 can prevent the cover 118 from coming off unexpectedly.

This bar code 116 has identification information for identifying the collected blood sample and corresponds to the identification mark of the present invention. In this embodiment, an adhesive layer is formed on the back surface of the bar code 116, and the bar code 116 is affixed to the surface of the attachment portion 117. Also, the cover 118 is transparent, and the bar code 116 attached to the attachment portion 117 can be optically read over the cover 118.

Also, a thread groove portion 120 threadedly engaged with the thread portion 106 of the bottomed tube 101 is provided in the lower portion of the inner peripheral surface of the cryopreservation cap 103 (see FIG. 2). This thread groove portion 120 is provided on the inner peripheral surface of the cryopreservation cap 103 and corresponds to the cap side thread portion of the present invention.

The above thread groove portion 120 is provided at a position that corresponds to the thread portion 106 of the bottomed tube 101 when the cryopreservation cap 103 is attached to the bottomed tube 101 (see FIG. 7). In other words, the cryopreservation cap 103 is configured so that the cryopreservation cap 103 can be threadedly attached to the bottomed tube 101.

A sealing member 121 is attached inside the cryopreservation cap 103. A fitting groove 122 having an outer diameter generally equal to the outer diameter of the sealing member 121 is formed on the inner peripheral surface of the cryopreservation cap 103 (see FIG. 2). The sealing member 121 is fitted in this fitting groove 122 (see FIG. 7). The outer diameter of this sealing member 121 is set to be slightly larger than the outer diameter of the opening 105 of the bottomed tube 101. A convex sealing portion 123 having an outer diameter generally equal to the inner diameter of the opening 105 of the bottomed tube 101 is provided on the lower surface of the sealing member 121.

As shown in FIG. 7, when the cryopreservation cap 103 is threadedly attached to the bottomed tube 101, the sealing member 121 seals the opening 105 of the bottomed tube 101, so that the liquid tight state of the vacuum blood collection tube 100 is maintained. This cryopreservation cap 103 is composed of a low temperature resistant material. In this embodiment, the same low temperature resistant material is used for the bottomed tube 101 and the cryopreservation cap 103 of the vacuum blood collection tube 100. Therefore, the thermal shrinkage rate during cooling is the same, so that the liquid tight state of the vacuum blood collection tube 100 can be maintained either at room temperature or at ultra-low temperature.

A method of manufacturing the vacuum blood collection tube 100 configured as described above will be described.

When the vacuum blood collection tube 100 in the first embodiment is manufactured, the operation of attachment of the stopper 102 to the bottomed tube 101 is performed in a reduced pressure chamber. In this embodiment, the blood coagulation preventing agent 109 is previously placed in the bottomed tube 101. Then, the needle piercing member 111 is attached to the opening 105 of the bottomed tube 101, and the cap member 112 is attached over the needle piercing member 111. In this case, the stopper convex portion 114 of the needle piercing member 111 fits suitably in the opening 105 of the bottomed tube 101, and the needle piercing member 111 is in close contact with the opening 105 of the bottomed tube 101, so that the reduced pressure state inside the bottomed tube 101 is maintained even at atmospheric pressure. Thus, the vacuum blood collection tube 100 as shown in FIG. 3 and FIG. 4 is manufactured.

Next, the operation when blood collection is performed using the above vacuum blood collection tube 100 will be described.

When blood collection is performed using the vacuum blood collection tube 100 in this embodiment, one end of the blood collection needle 110 is inserted into a blood vessel of a subject, and then, the other end of the blood collection needle 110 is pierced into the needle piercing member 111 of the stopper 102, as shown in FIG. 5. Then, due to the pressure difference between the pressure inside the blood vessel and the pressure inside the bottomed tube 101, the collection of blood from the subject is performed.

When the blood collection needle 110 is pulled out after blood collection, the needle piercing member 111 is elastically deformed to close the needle hole, so that liquid tightness is kept. Thus, the collected blood sample is prevented from leaking from the needle hole made during blood collection.

Next, the operation when cryopreservation is performed after blood collection will be described.

When the cryopreservation of the collected blood sample is performed after blood collection is performed using the vacuum blood collection tube 100 in this embodiment, the stopper 102 is removed from the bottomed tube 101, and the cryopreservation cap 103 is attached to the bottomed tube 101. In other words, the stopper 102 and the cryopreservation cap 103 are exchanged.

As shown in FIG. 6 and FIG. 7, when the cryopreservation cap 103 is threadedly attached to the bottomed tube 101, the convex sealing portion 123 of the sealing member 121 fits suitably in the opening 105 of the bottomed tube 101, and the opening 105 of the bottomed tube 101 is sealed by the sealing member 121. Thus, the liquid tightness of the bottomed tube 101 is maintained. Then, the vacuum blood collection tube 100 is stored in a cryopreservation chamber. Thus, the vacuum blood collection tube 100 is cryopreserved at ultra-low temperature as it is, without transferring the collected blood sample to another blood storage container.

According to such a vacuum blood collection tube 100 in the first embodiment, the collected blood sample can be cryopreserved at ultra-low temperature as it is, without being transferred to another blood storage container, so that effort and burden on an operator can be significantly reduced.

In other words, in this embodiment, before blood collection, the stopper 102 is attached to the opening 105 of the bottomed tube 101, and the stopper 102 is in close contact with the opening 105 of the bottomed tube 101, so that the reduced pressure state inside the bottomed tube 101 is maintained. During blood collection, one end of the blood collection needle 110 is inserted into a blood vessel of a subject, and then, the other end of the blood collection needle 110 is pierced into the needle-piercing portion 113. Then, due to the pressure difference between the pressure inside the blood vessel and the pressure inside the bottomed tube 101, the collection of blood from the subject is performed. Thus, blood collection can be performed by a vacuum blood collection method.

After blood collection, the cryopreservation cap 103 is attached to the opening 105 of the bottomed tube 101, and the opening 105 of the bottomed tube 101 is sealed, so that the liquid tight state of the bottomed tube 101 is maintained. In this case, the bottomed tube 101 and the cryopreservation cap 103 are composed of a low temperature resistant material that is less susceptible to low temperature fracture when cryopreserved at ultra-low temperature. Thus, the vacuum blood collection tube 100 having the cryopreservation cap 103 attached has the function of a blood storage container for cryopreservation at ultra-low temperature. Therefore, a blood storage container for cryopreservation that can endure preservation at ultra-low temperature need not be separately prepared. Also, the collected blood sample can be cryopreserved at ultra-low temperature as it is, without being transferred to another blood storage container. Thus, effort and burden on the operator are significantly reduced.

Also, in this embodiment, after blood collection, the stopper 102 is removed from the opening 105 of the bottomed tube 101, and the cryopreservation cap 103 is attached to the opening 105 of the bottomed tube 101, in exchange of the stopper 102. Thus, the opening 105 of the bottomed tube 101 is sealed, so that the liquid tight state of the bottomed tube 101 is maintained. Thus, the vacuum blood collection tube 100 having the cryopreservation cap 103 attached has the function of a blood storage container for cryopreservation at ultra-low temperature. In other words, it can also be said that the vacuum blood collection tube 100 in this embodiment has both the function of the normal vacuum blood collection tube 100 and the function of a blood storage container for cryopreservation.

Also, in this embodiment, the stopper 102 of the vacuum blood collection tube 100 is composed of two members, the needle piercing member 111 and the cap member 112. Therefore, compared with a case where the stopper 102 is composed of one member, the stopper 102 can be manufactured relatively easily even if the configuration of the needle piercing member 111 and the cap member 112 is complicated.

Also, in this embodiment, when the cryopreservation cap 103 is attached to the opening 105 of the bottomed tube 101 after blood collection, the thread groove portion 120 on the inner peripheral surface of the cold preservation cap is threadedly engaged with the thread portion 106 on the outer peripheral surface of the bottomed tube 101. Thus, by threadedly attaching the cryopreservation cap 103 to the bottomed tube 101, the opening 105 of the bottomed tube 101 is tightly sealed, so that the liquid tightness of the bottomed tube 101 can be enhanced.

Also, in this embodiment, the stopper 102 of the vacuum blood collection tube 100 is attached to the thread absent portion 107 on the outer peripheral surface of the bottomed tube 101. Therefore, the thread portion 106 of the bottomed tube 101 is prevented from becoming an obstacle when the stopper 102 is attached to the opening 105 of the bottomed tube 101. Therefore, the stopper 102 can be smoothly attached to the bottomed tube 101.

In this case, the bar code 116 is attached to the upper surface of the bottomed tube 101, but it is desired that the bar code 116 is also attached to the side of the bottomed tube 101. But, in the case where the bar code 116 is attached to the side of the bottomed tube 101, when a large number of the vacuum blood collection tubes 100 are placed vertically in a rack, read operation should be performed by a bar code reader while the vacuum blood collection tubes 100 are taken out one by one, so that the read operation is complicated. On the other hand, in this embodiment, the bar code 116, in which it is previously confirmed that the same code as the bar code on the side is recorded, is attached to the upper surface of the bottomed tube 101. Therefore, even if a large number of the vacuum blood collection tubes 100 are placed vertically in a rack, the operation of confirming the vacuum blood collection tube 100 (the read operation using the bar code reader) is very easy.

Also, in this embodiment, the bar code 116 is affixed to the attachment portion 117 of the cryopreservation cap 103. The bar code 116 affixed to the attachment portion 117 is covered with the transparent cover 118 and protected. Therefore, the bar code 116 can be prevented from being damaged by liquid nitrogen, nitrogen bubbles, and physical factors. Also, the identification mark covered with this cover 118 can be externally optically read. Therefore, by optically reading sample identification information written in the bar code 116, the collected blood sample can be easily identified. Thus, the occurrence of sample mix-up can be suppressed.

In this case, the stopper 102 is fitted on and attached to the bottomed tube 101, but the stopper 102 may be inserted into and attached to the bottomed tube 101. Currently, many of apparatuses for manufacturing the vacuum blood collection tube 100 address the fitted-on type vacuum blood collection tube 100. Therefore, if a threaded-in type in which the stopper 102 is inserted into the bottomed tube 101 is used, the current manufacturing apparatus cannot be used as it is, so that an insertion type (threaded-in type) manufacturing apparatus should be redeveloped again, and an increase in manufacturing cost is expected. On the other hand, in this embodiment, the fitted-on type vacuum blood collection tube 100 is used, and the thread portion 106 is located at a position where the thread portion 106 does not become an obstacle when the stopper 102 is attached, so that the vacuum blood collection tube 100 can be manufactured using the previous manufacturing apparatus as it is.

Also, in this embodiment, the thin film 108 having a gas barrier property is formed on the inner peripheral surface of the bottomed tube 101, so that the airtightness of the bottomed tube 101 is improved. Therefore, the reduced pressure state inside the bottomed tube 101 can be maintained for a long period.

Also, in this embodiment, the blood coagulation preventing agent 109 is placed in the bottomed tube 101, so that when blood is collected using the vacuum blood collection tube 100, the collected blood immediately comes into contact with the blood coagulation preventing agent 109. Therefore, the blood coagulation preventing agent 109 immediately acts on the collected blood sample, so that the coagulation of the blood sample can be prevented.

Second Embodiment

Next, a vacuum blood collection tube in the second embodiment of the present invention will be described using FIG. 8 to FIG. 15. Here, description is given focusing on points where the vacuum blood collection tube in this embodiment is different from that in the first embodiment. Therefore, unless otherwise specified here, the configuration of this embodiment is similar to that of the first embodiment.

Figure 8:
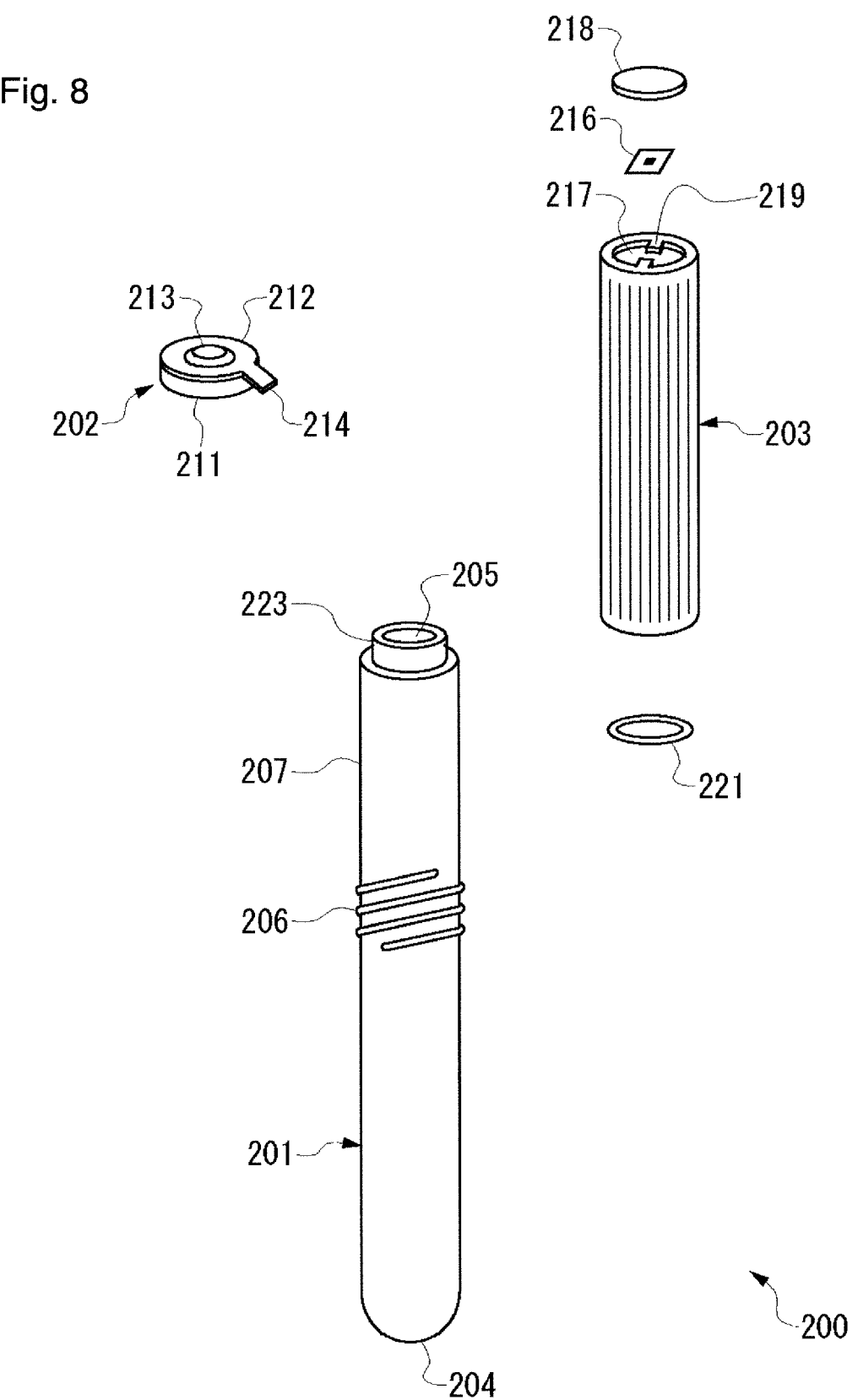
FIG. 8 is a perspective view of a vacuum blood collection tube (a bottomed tube, a stopper, and a cryopreservation cap) in a second embodiment.

FIG. 8 is a perspective view showing the configuration of the vacuum blood collection tube, and FIG. 9 is a cross-sectional view showing the configuration of the vacuum blood collection tube. As shown in FIG. 8 and FIG. 9, a vacuum blood collection tube 200 comprises a bottomed tube 201, a stopper 202, and a cryopreservation cap 203. In the vacuum blood collection tube 200 in this embodiment, the cryopreservation cap 203 is attached to the bottomed tube 201 over the stopper 202 (covering the stopper 202).

The bottomed tube 201 is generally cylindrical and has a bottom portion 204 at one end and an opening 205 at the other end. A thread portion 206 and a thread absent portion 207 are provided on the outer peripheral surface of the bottomed tube 201, as in the first embodiment. In this embodiment, a fitting step portion 223 to which the stopper 202 is fitted is provided at the end of the bottomed tube 201 on the opening 205 side (see FIG. 8 and FIG. 9). It can also be said that this fitting step portion 223 is the small diameter part of the bottomed tube 201 on the opening 205 side. Also, this bottomed tube 201 is composed of a low temperature resistant material, as in the first embodiment.

Figure 10:
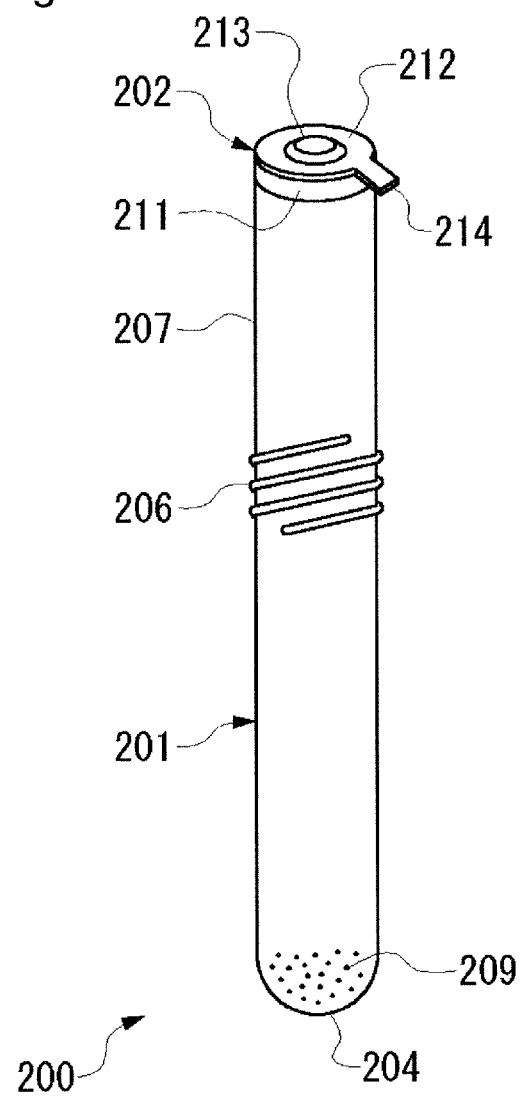
FIG. 10 is a perspective view of the vacuum blood collection tube before blood collection.
Figure 11:
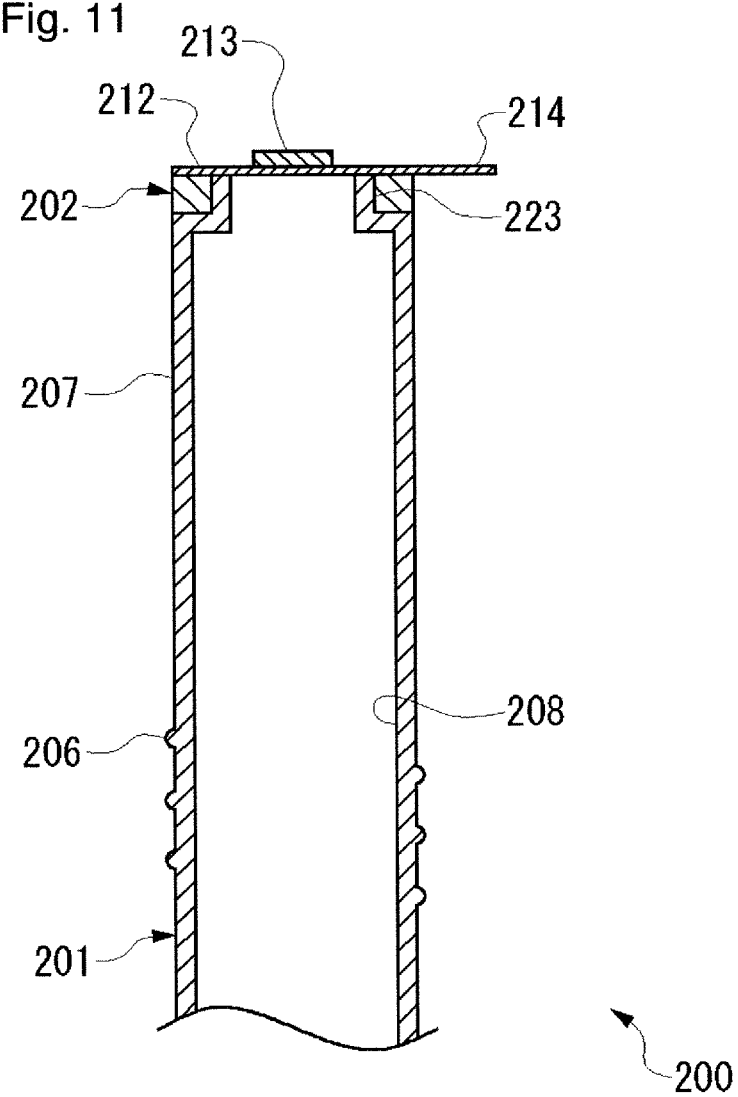
FIG. 11 is an enlarged cross-sectional view of the vacuum blood collection tube before blood collection.
Figure 12:
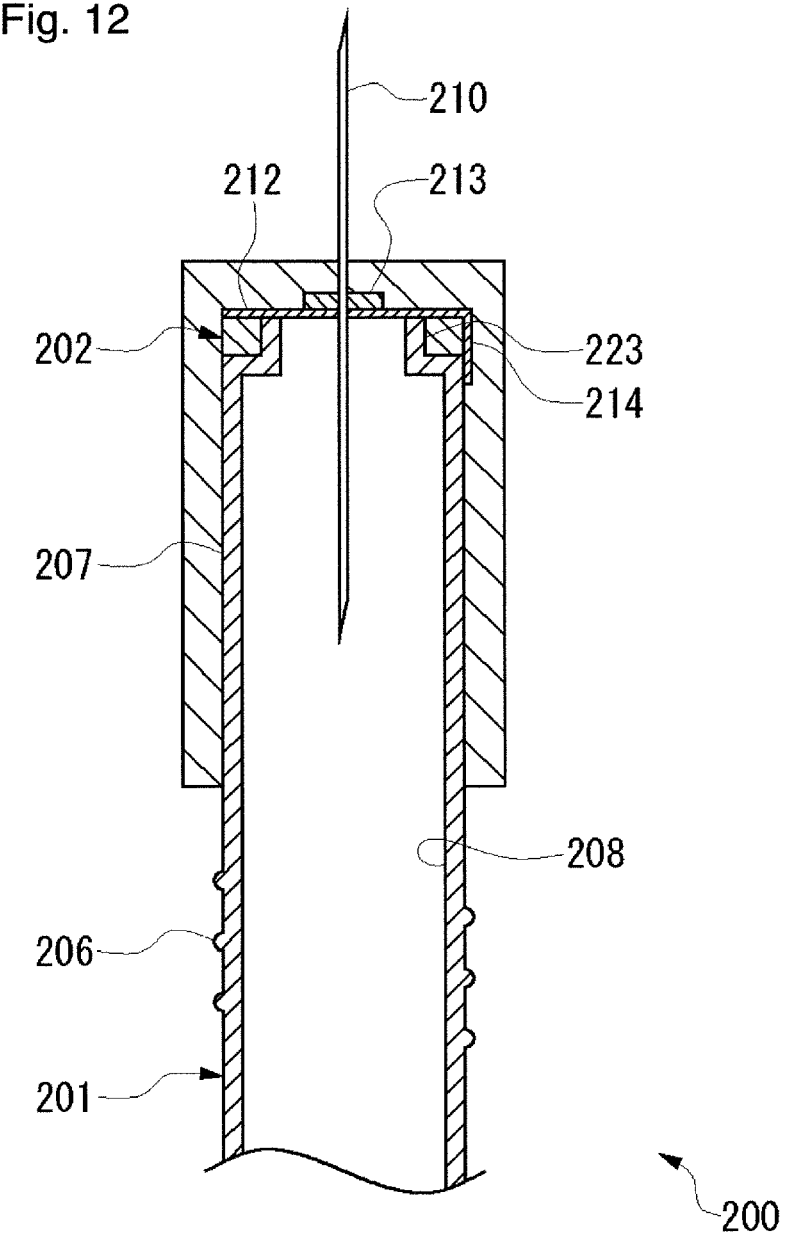
FIG. 12 is an enlarged cross-sectional view of the vacuum blood collection tube during blood collection.

FIG. 10 is a perspective view of the vacuum blood collection tube 200 before blood collection, and FIG. 11 is a cross-sectional view of the vacuum blood collection tube 200 before blood collection. FIG. 12 is a cross-sectional view schematically showing the vacuum blood collection tube 200 during blood collection. As shown in FIG. 10 and FIG. 11, the stopper 202 is attached to the fitting step portion 223 of the bottomed tube 201 before blood collection.

The stopper 202 comprises an annular main body 211, and a seal member 212 affixed to the upper surface of the main body 211. In this case, it can also be said that a needle insertion hole 215 through which a blood collection needle 210 is inserted is provided in the central portion of the main body 211. A needle piercing portion 213 composed of a rubber material that can be pierced with the blood collection needle 210 is provided in the center of the seal member 212. Also, a handle piece 214 that is a hold when the seal member 212 is peeled off is provided at an end of the seal member 212 (see FIG. 15).

As shown in FIG. 10 and FIG. 11, when the stopper 202 is attached to the fitting step portion 223 of the bottomed tube 201, the stopper 202 is in close contact with the opening 205 of the bottomed tube 201, so that the airtightness inside the bottomed tube 201 can be kept.

In the vacuum blood collection tube 200 before blood collection, the pressure is reduced inside the bottomed tube 201. In this case, the stopper 202 is in close contact with the bottomed tube 201, so that airtightness is kept, therefore, due to the pressure difference between the air pressure inside the bottomed tube 201 and atmospheric pressure, the stopper 202 is pressed against the bottomed tube 201. Thus, the reduced pressure state inside the bottomed tube 201 before blood collection is maintained.

Figure 13:
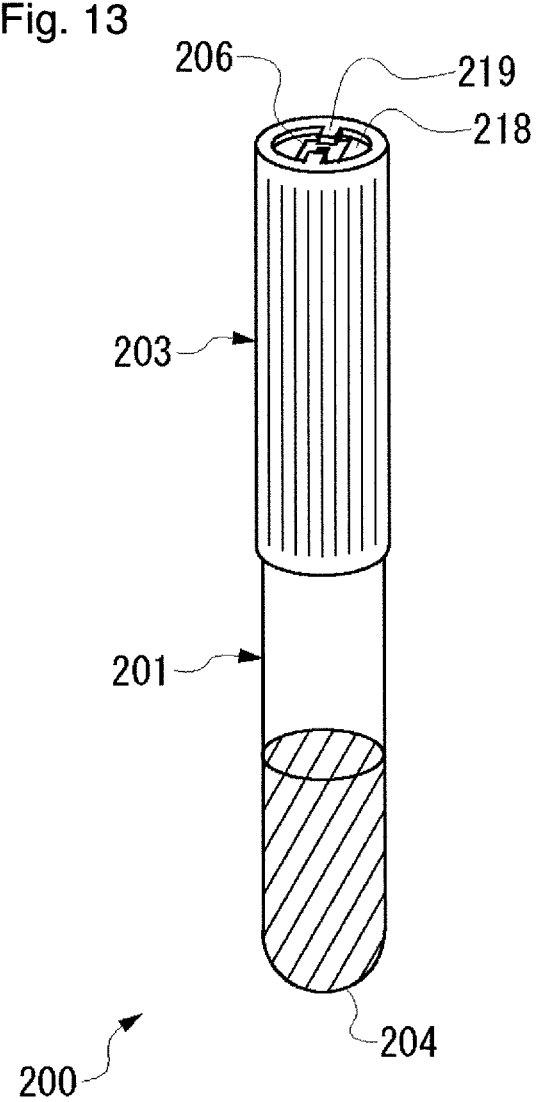
FIG. 13 is a perspective view of the vacuum blood collection tube after blood collection (during cryopreservation)
Figure 14:
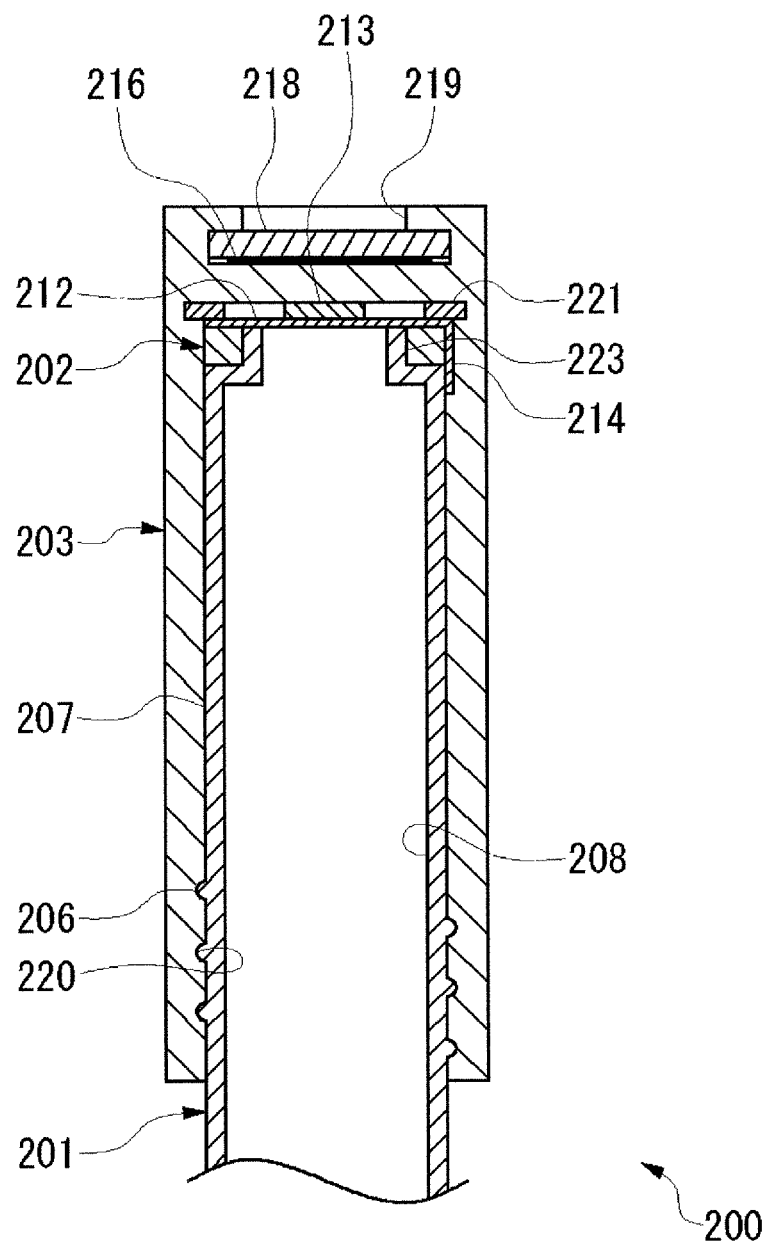
FIG. 14 is an enlarged cross-sectional view of the vacuum blood collection tube after blood collection (during cryopreservation)
Figure 15:
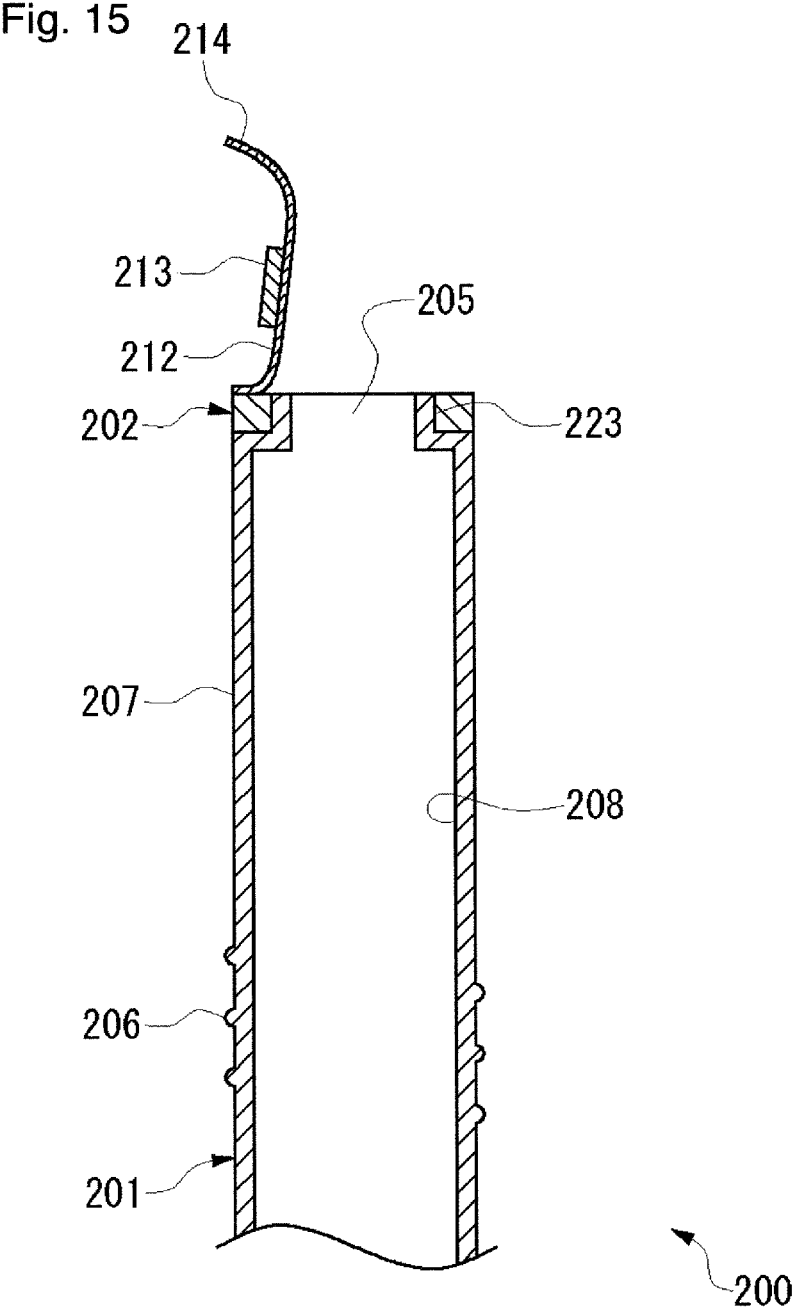
FIG. 15 is an enlarged cross-sectional view of the vacuum blood collection tube when a collected blood sample is removed.

FIG. 13 is a perspective view of the vacuum blood collection tube 200 at the time of cryopreservation after blood collection, and FIG. 14 is a cross-sectional view of the vacuum blood collection tube 200 at the time of cryopreservation after blood collection. As shown in FIG. 13 and FIG. 14, the cryopreservation cap 203 is attached to the opening 205 of the bottomed tube 201 when the collected blood is cryopreserved. In this embodiment, the cryopreservation cap 203 is attached to the opening 205 of the bottomed tube 201, covering the stopper 202, after blood collection.

The cryopreservation cap 203 is generally cylindrical, and an attachment portion 217 to which an IC tag 216 is attached is concavely provided on the upper surface of the cryopreservation cap 203 (see FIG. 8). A cover 218 covering the IC tag 216 is attached to the attachment portion 217. Also, a pair of projecting press pieces 219 as in the first embodiment is provided in the attachment portion 217.

This IC tag 216 has identification information for identifying the collected blood sample and corresponds to the identification mark of the present invention. In this embodiment, an adhesive layer is formed on the back surface of the IC tag 216, and the IC tag 216 is affixed to the surface of the attachment portion 217. Also, the cover 218 is composed of a radio wave transmitting material (material not having an electromagnetic shielding property), and radio wave communication with the IC tag 216 attached to the attachment portion 217 is possible over the cover 218.

A thread groove portion 220 as in the first embodiment is provided in the lower portion of the inner peripheral surface of the cryopreservation cap 203 (see FIG. 9). Also, an O-ring 221 is attached inside the cryopreservation cap 203. A fitting groove 222 having an outer diameter generally equal to the outer diameter of the O-ring 221 is formed on the inner peripheral surface of the cryopreservation cap 203 (see FIG. 9). The O-ring 221 is fitted in this fitting groove 222 (see FIG. 14). The outer diameter of this O-ring 221 is set to be slightly larger than the outer diameter of the bottomed tube 201, and the inner diameter of the O-ring 221 is set to be slightly smaller than the outer diameter of the bottomed tube 201.

As shown in FIG. 14, when the cryopreservation cap 203 is threadedly attached to the bottomed tube 201, the O-ring 221 seals the bottomed tube 201, so that the liquid tight state of the vacuum blood collection tube 200 is maintained. The cryopreservation cap 203 is composed of a low temperature resistant material as in the first embodiment.

A method of manufacturing the vacuum blood collection tube 200 configured as described above will be described.

When the vacuum blood collection tube 200 in the second embodiment is manufactured, the operation of attachment of the stopper 202 to the bottomed tube 201 is performed in a reduced pressure chamber. In this embodiment, a blood coagulation preventing agent 209 is previously placed in the bottomed tube 201, and then, the stopper 202 is attached to the opening 205 of the bottomed tube 201. In this case, the main body 211 of the stopper 202 fits suitably to the fitting step portion 223 of the bottomed tube 201, and the stopper 202 is in close contact with the opening 205 of the bottomed tube 201, so that the reduced pressure state inside the bottomed tube 201 is maintained even at atmospheric pressure. Thus, the vacuum blood collection tube 200 as shown in FIG. 10 and FIG. 11 is manufactured.

Next, the operation when blood collection is performed using the above vacuum blood collection tube 200 will be described.

When blood collection is performed using the vacuum blood collection tube 200 in this embodiment, one end of the blood collection needle 210 is inserted into a blood vessel of a subject, and then, the other end of the blood collection needle 210 is pierced into the needle piercing portion 213 of the stopper 202, as shown in FIG. 12. Then, due to the pressure difference between the pressure inside the blood vessel and the pressure inside the bottomed tube 201, the collection of blood from the subject is performed.

When the blood collection needle 210 is pulled out after blood collection, the needle piercing portion 213 is elastically deformed to close the needle hole, so that liquid tightness is kept. Thus, the collected blood sample is prevented from leaking from the needle hole made during blood collection.

Next, the operation when cryopreservation is performed after blood collection will be described.

When the cryopreservation of the collected blood sample is performed after blood collection is performed using the vacuum blood collection tube 200 in this embodiment, the cryopreservation cap 203 is attached without removing the stopper 202 from the bottomed tube 201. In other words, the cryopreservation cap 203 is attached over the stopper 202.

As shown in FIG. 13 and FIG. 14, when the cryopreservation cap 203 is threadedly attached to the bottomed tube 201, the bottomed tube 201 is sealed by O-ring 221, so that the liquid tightness of the bottomed tube 201 is maintained. Then, the vacuum blood collection tube 200 is stored in a cryopreservation chamber. Thus, the vacuum blood collection tube 200 is cryopreserved at ultra-low temperature as it is, without transferring the collected blood sample to another blood storage container.

The action and effect as in the first embodiment can also be obtained by such a vacuum blood collection tube 200 in the second embodiment.

In this embodiment, after blood collection, the cryopreservation cap 203 is attached to the opening 205 of the bottomed tube 201, covering the stopper 202, without removing the stopper 202 from the opening 205 of the bottomed tube 201. Thus, the opening 205 of the bottomed tube 201 is sealed, so that the liquid tight state of the bottomed tube 201 is maintained. Thus, the vacuum blood collection tube 200 having the cryopreservation cap 203 attached has the function of a blood storage container for cryopreservation at ultra-low temperature. In other words, it can also be said that the vacuum blood collection tube 200 in this embodiment has both the function of the normal vacuum blood collection tube 200 and the function of a blood storage container for cryopreservation. In this case, the stopper 202 needs not be removed after blood collection, so that the scattering of the blood sample in removing the stopper 202, and the resulting contamination can be prevented.

Also, in this embodiment, the IC tag 216 is attached to the attachment portion 217 of the cryopreservation cap 203. The IC tag 216 attached to the attachment portion 217 is covered with the radio wave transmitting cover 218 and protected. In other words, the IC tag 216 can be protected from freezing and physical damage. Also, the IC tag 216 covered with this cover 218 can be externally read via radio wave communication. Therefore, by reading sample identification information written in the IC chip of the IC tag 216, via radio wave communication, the collected blood sample can be easily identified. Thus, the occurrence of sample mix-up can be suppressed.

Third Embodiment

Next, a vacuum blood collection tube in the third embodiment of the present invention will be described using FIG. 16 and FIG. 17. Here, description is given focusing on points where the vacuum blood collection tube in this embodiment is different from that in the first embodiment. Therefore, unless otherwise specified here, the configuration of this embodiment is similar to that of the first embodiment.

Figure 16:
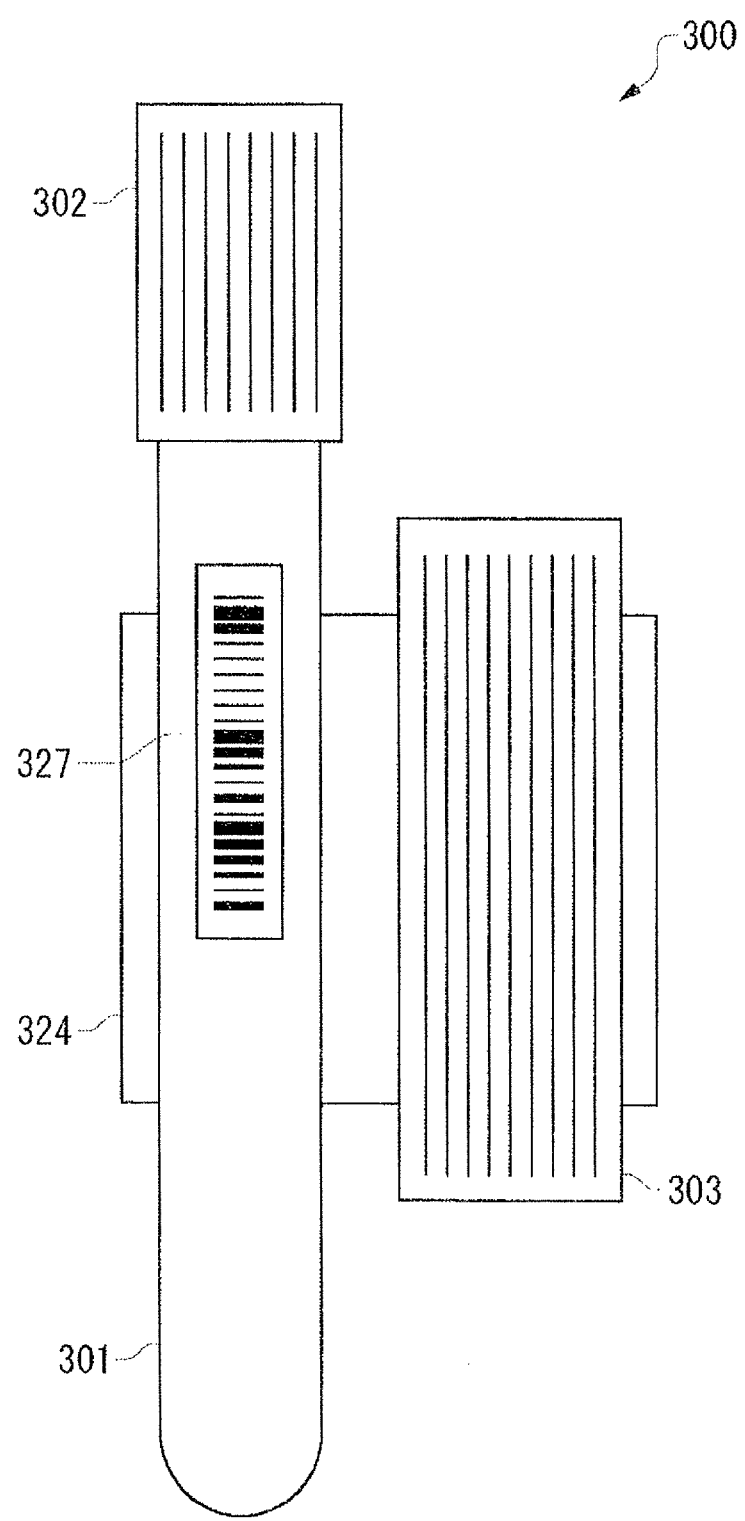
FIG. 16 is a plan view of a vacuum blood collection tube set (a bottomed tube, a stopper, and a cryopreservation cap) in a third embodiment.

FIG. 16 is a plan view showing a vacuum blood collection tube set. As shown in FIG. 16, in this embodiment, a bottomed tube 301 to which a stopper 302 is attached, and a cryopreservation cap 303 are connected by a connection part 324. In this case, it can also be said that the bottomed tube 301 to which the stopper 302 is attached, and the cryopreservation cap 303 constitute a vacuum blood collection tube 300 set (also referred to as a vacuum blood collection tube set) with the connection part 324.

Figure 17:
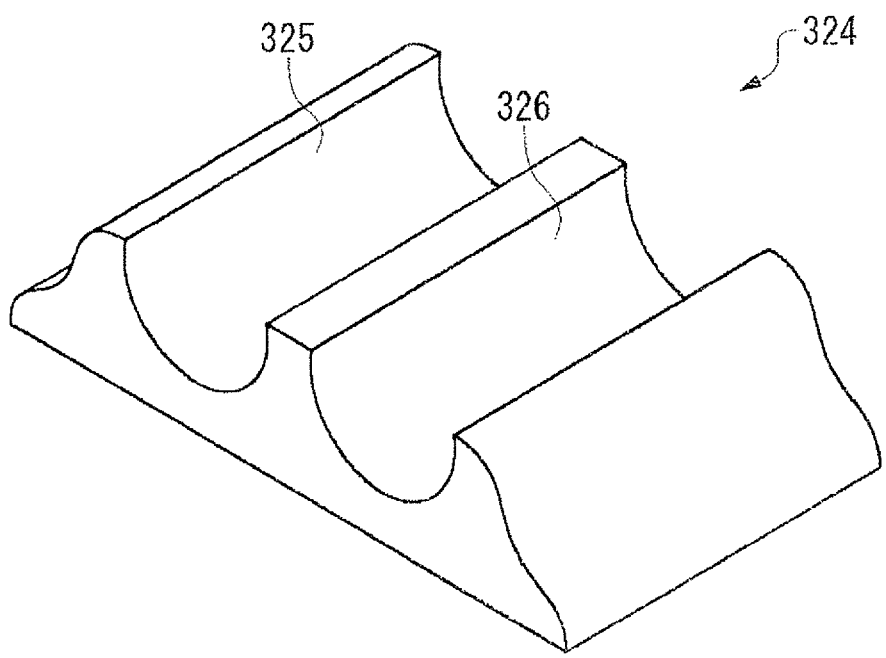
FIG. 17 is a perspective view showing one example of a connection part.

FIG. 17 is a perspective view showing one example of the connection part 324. As shown in FIG. 17, a first holding concave portion 325 for holding the bottomed tube 301, and a second holding concave portion 326 for holding the cryopreservation cap 303 are provided in the connection part 324. By fitting the bottomed tube 301 into the first holding concave portion 325 of this connection part 324 and fitting the cryopreservation cap 303 into the second holding concave portion 326, the vacuum blood collection tube 300 is packaged in one package (not shown) and supplied, with the bottomed tube 301 and the cryopreservation cap 303 connected (see FIG. 16).

At this time, a bar code 327 (set identification mark) for identifying the vacuum blood collection tube set is applied to each of the bottomed tube 301 and the cryopreservation cap 303 constituting the vacuum blood collection tube set. For example, the bar code seal 327 for identifying the vacuum blood collection tube set is affixed to the side of the bottomed tube 301 (see FIG. 16). Also, a bar code 316 for identifying the vacuum blood collection tube set is attached to the upper surface of the cryopreservation cap 303, as in the first embodiment (see FIG. 19). The vacuum blood collection tube 300 is supplied, with the bottomed tube 301 and the cryopreservation cap 303 being clearly shown as a set, using the bar codes 327 and 316, in this manner. Here, the bar code may be not only a one-dimensional bar code, such as JAN (FAN and UPC), ITF, CODE39, NW-7 (CODABAR), and CODE128, but also a two-dimensional bar code, such as QR CODE, Micro QR Code49, PDF417, Veri Code, and Data Matrix, RF-ID, and the like.

For example, in a clinical trial, such as a PGx test, from which individual a sample is provided should be concealed. Therefore, a number that cannot specify an individual is often given to the vacuum blood collection tube 300, without writing a name or address that can specify the individual, for management. This number is generally directly provided on the vacuum blood collection tube 300, or turned into a bar code, a seal of which is affixed to the vacuum blood collection tube 300.

In this embodiment, the bar codes 327 and 316 are applied to both of the bottomed tube 301 and the cryopreservation cap 303, and it is ensured that their numbers are also the same during blood collection. When it is confirmed during the supply of the vacuum blood collection tube 300 that the numbers of the bottomed tube 301 and the cryopreservation cap 303 are the same, then, the bottomed tube 301 and the cryopreservation cap 303 are coupled by the connection part 324 until blood collection.

This connection part 324 is manufactured using an inexpensive material, such as polystyrene. Also, the connection part 324 desirably has a size as small as possible, considering disposal, and is desirably composed of an easily recycled material. The bottomed tube 301 and the cryopreservation cap 303 may be packaged in a polystyrene bag, instead of using the connection part 324.

Figure 18:
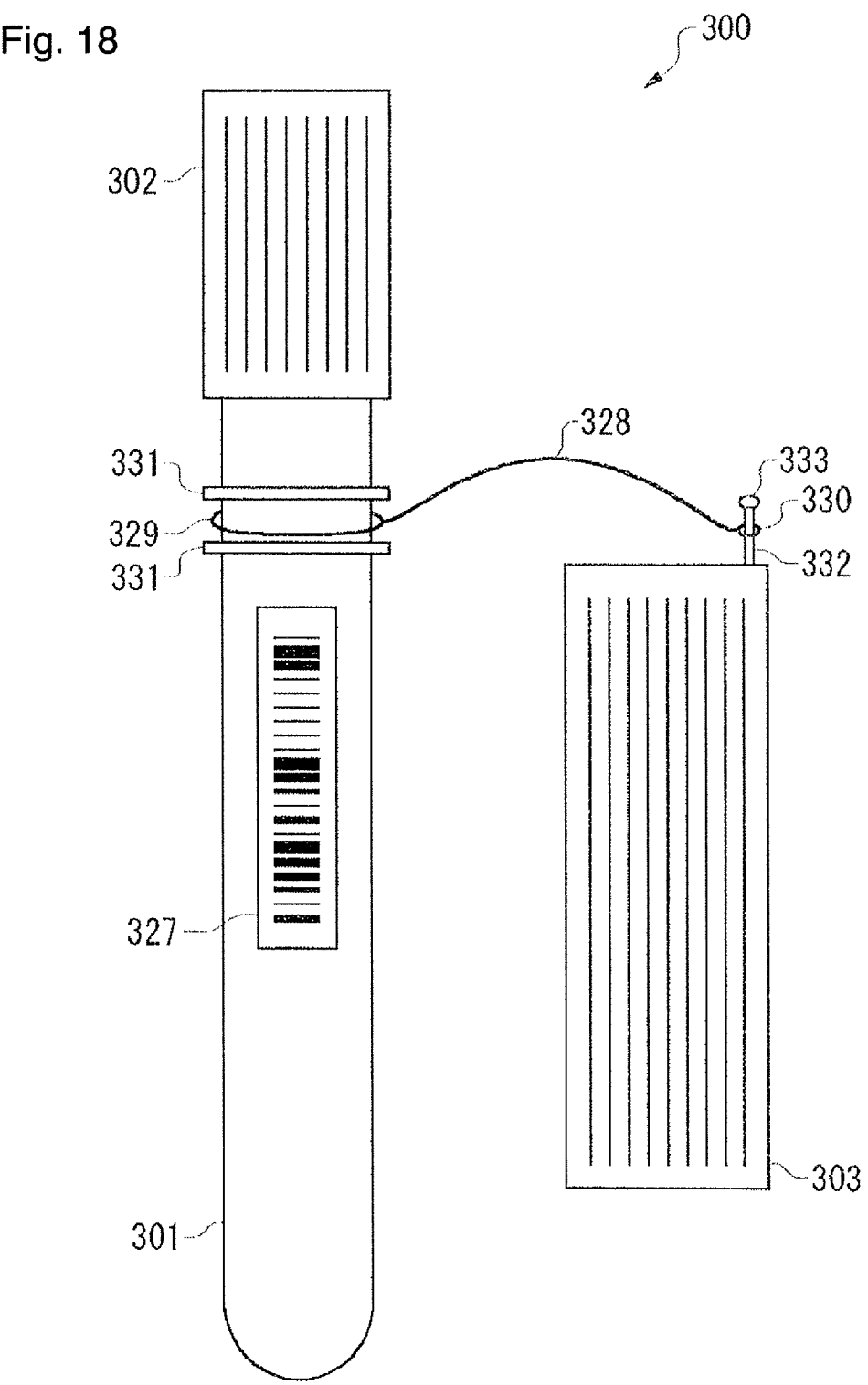
FIG. 18 is a plan view showing a modification of the connection part.
Figure 19:
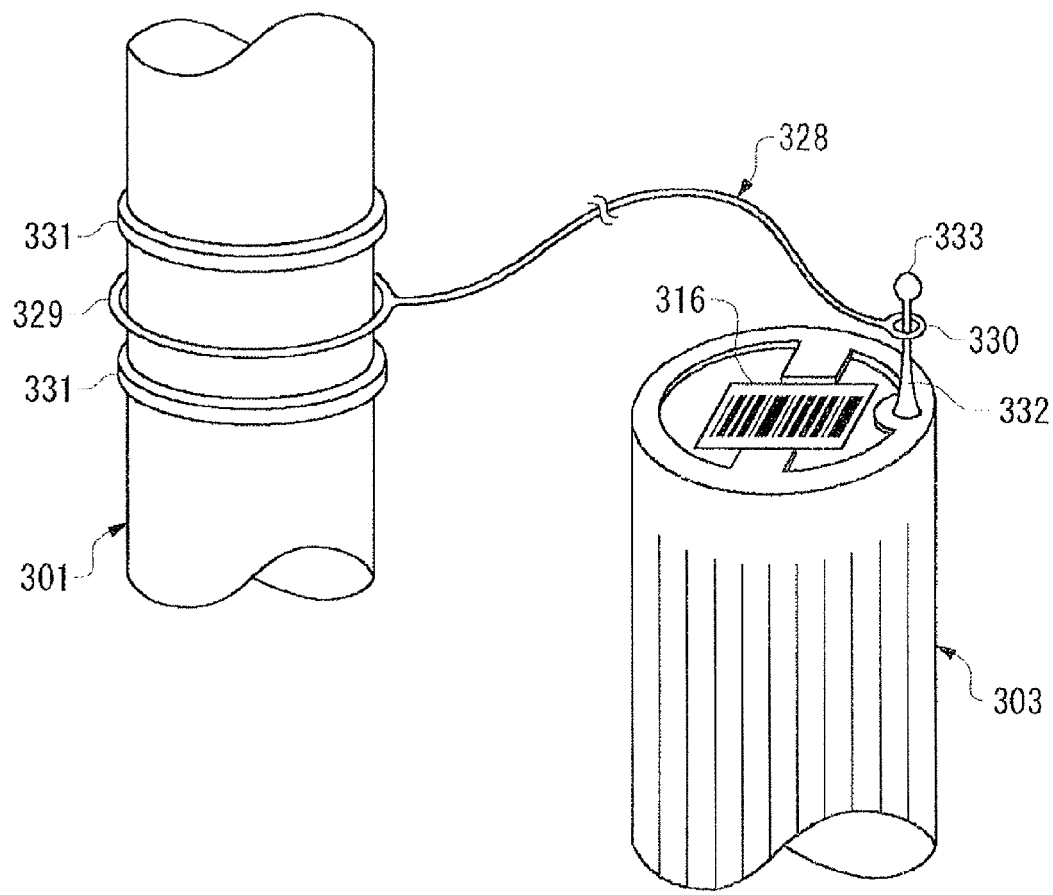
FIG. 19 is an enlarged perspective view of the modification of the connection part.

FIG. 18 is a plan view showing a modification of the connection part, and FIG. 19 is an enlarged perspective view of the modification of the connection part. As shown in FIG. 18 and FIG. 19, a connection part 328 may be a string-like one having a connection ring at both ends. A first connection ring of a size fitting suitably on the bottomed tube 301 is provided at one end of this connection part 328. Also, a second connection ring smaller than the first connection ring is provided at the other end of the connection part 328. Two ring stop convex portions 331 are provided on the bottomed tube 301, and the first connection ring is rotatably fitted between these two ring stop convex portions 331. On the other hand, a connection pin 333 having a slip-out preventing portion 332 at the tip is vertically provided at an end of the upper surface of the cryopreservation cap 303, and the second connection ring is rotatably fitted on this connection pin 333.

According to such a vacuum blood collection tube 300 in the third embodiment, the bottomed tube 301 and the cryopreservation cap 303 are connected, so that when a blood sample is collected, the trouble of looking for the cryopreservation cap 303 at the site of the operation of blood collection can be saved.

Also, in this embodiment, a common set identification mark (for example, a bar code) is applied to both of the bottomed tube 301 and the cryopreservation cap 303, so that the collected sample can be easily managed.

For example, after it is confirmed during the shipment of the vacuum blood collection tube 300 that the numbers of the bar codes 327 and 316 are the same, the sameness of the numbers can be ensured until blood collection and storage steps.

When the connection part 328 is string-like, the connection part 328 may be adhered or the like and fixed to the bottomed tube 301 and the cryopreservation cap 303. But, the cryopreservation cap 303 is rotated and attached to the bottomed tube 301, so that the connection part 328 is desirably rotatably attached to the cryopreservation cap 303. Also, as shown in FIG. 19, the bar code 316 can be attached to the central portion of the upper surface of the cryopreservation cap 303, so that the connection pin 333 is desirably provided at an end of the upper surface of the cryopreservation cap 303 to sufficiently obtain a place to which the bar code 316 is attached.

As the material of the connection parts 324 and 328, the same low temperature resistant material as that of the bottomed tube 301 and the cryopreservation cap 303 may be used, and a material having flexibility, such as silicon rubber, may be used.

Also, when a configuration in which the connection part 324 or 328 can be removed from the bottomed tube 301 and the cryopreservation cap 303 is used, the space for the preservation of the vacuum blood collection tube 300 can be reduced by removing the connection part 324 or 328 after attaching the cryopreservation cap 303 to the bottomed tube 301.

Fourth Embodiment

Next, a vacuum blood collection tube in the fourth embodiment of the present invention will be described using FIG. 20. Here, description is given focusing on points where the vacuum blood collection tube in this embodiment is different from that in the third embodiment. Therefore, unless otherwise specified here, the configuration of this embodiment is similar to that of the third embodiment.

Figure 20:
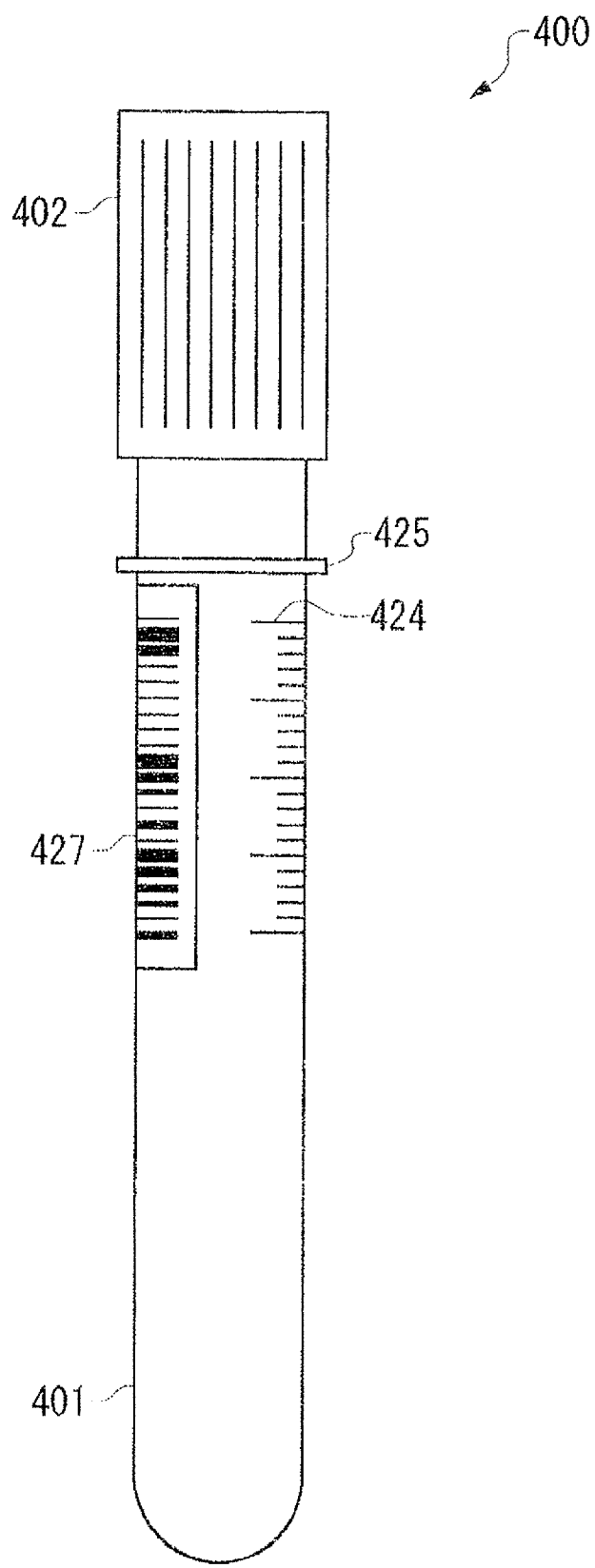
FIG. 20 is a plan view of a vacuum blood collection tube (a bottomed tube and a cryopreservation cap) in a fourth embodiment.

FIG. 20 is a plan view of the vacuum blood collection tube (a bottomed tube and a cryopreservation cap) in the fourth embodiment. As shown in FIG. 20, a scale 424 for measuring the amount of a collected sample is provided on the outer peripheral surface of a bottomed tube 401.

For example, in PGx or a clinical trial, the amount of collected blood should sometimes be recorded according to a protocol. Also, the amount of collected blood should often be described in a report in monitoring a blood collection method. In such cases, the amount of the collected blood sample is measured using the scale 424 of the bottomed tube 401. This scale 424 may be formed on the bottomed tube 401 by printing, and may be formed on the bottomed tube 401 by convex processing.

Also, as shown in FIG. 20, an annular affixing guide portion 425 is convexly provided on the outer peripheral surface of the bottomed tube 401. This affixing guide portion 425 is a reference line for affixing a bar code seal 427 (sample identification mark seal) for identifying a collected sample. In this case, by affixing the bar code seal 427 along the affixing guide portion 425, the bar code seal 427 can be affixed parallel to the axial direction of the bottomed tube 401.

For example, in PGx or a clinical trial, the bar code seal 427 can be affixed to a vacuum blood collection tube 400 to identify a sample. The shape of the bar code seal 427 is often rectangular, but skill is required to affix the rectangular bar code seal 427 parallel to the axial direction of the bottomed tube 401. If the bar code seal 427 is affixed obliquely to the axial direction of the bottomed tube 401, due to the displacement between the direction of reading the bar code 427 and the direction of affixing the bar code 427, a bar code 427 reading error may occur.

In this embodiment, the affixing guide portion 425 is provided on the bottomed tube 401, so that by using the affixing guide portion 425 as a reference, the bar code seal 427 can be easily affixed parallel to the axial direction of the bottomed tube 401. This affixing guide portion 425 also may be formed on the bottomed tube 401 by printing, and may be formed on the bottomed tube 401 by convex processing.

Figure 21:
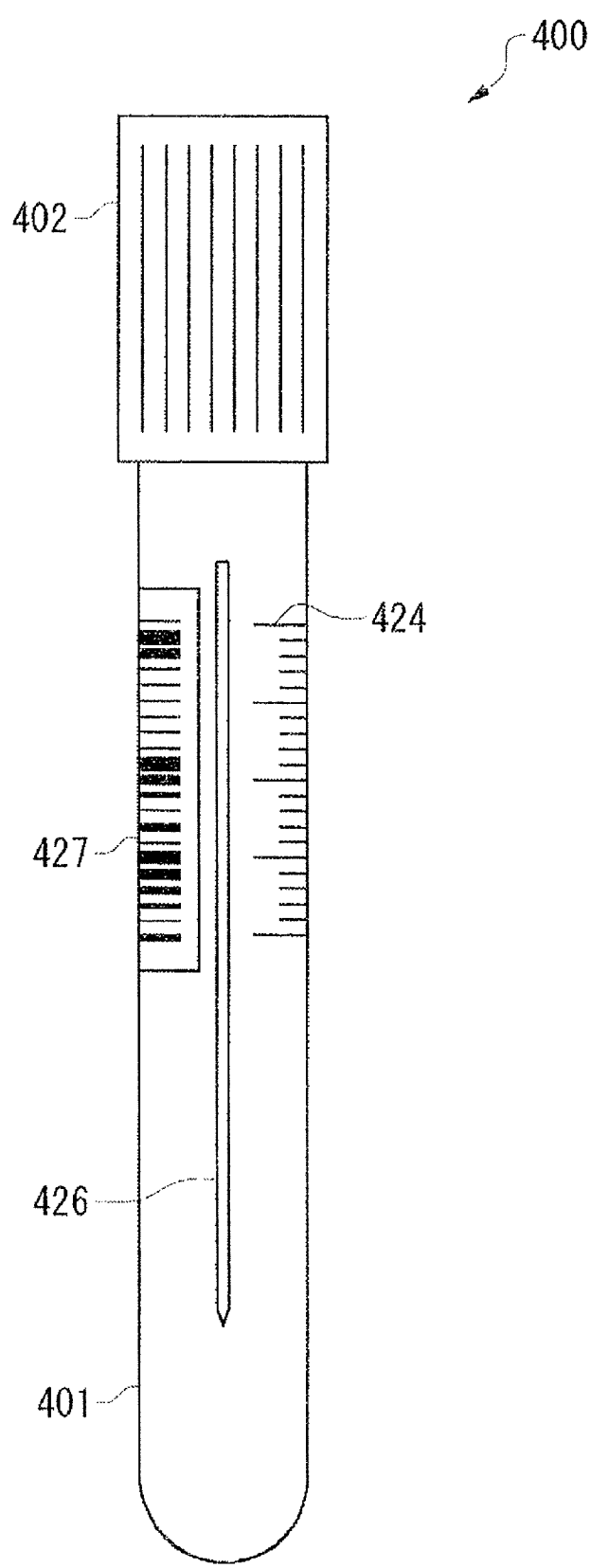
FIG. 21 is a plan view showing a modification of the vacuum blood collection tube in the fourth embodiment.

FIG. 21 is a plan view showing a modification of the vacuum blood collection tube 400 in the fourth embodiment. In this modification, the affixing guide portion 425 may be provided along the axial direction of the bottomed tube 401. Also when such an affixing guide portion 425 is used as a reference, the bar code seal 427 can be easily affixed parallel to the axial direction of the bottomed tube 401.

Figure 22:
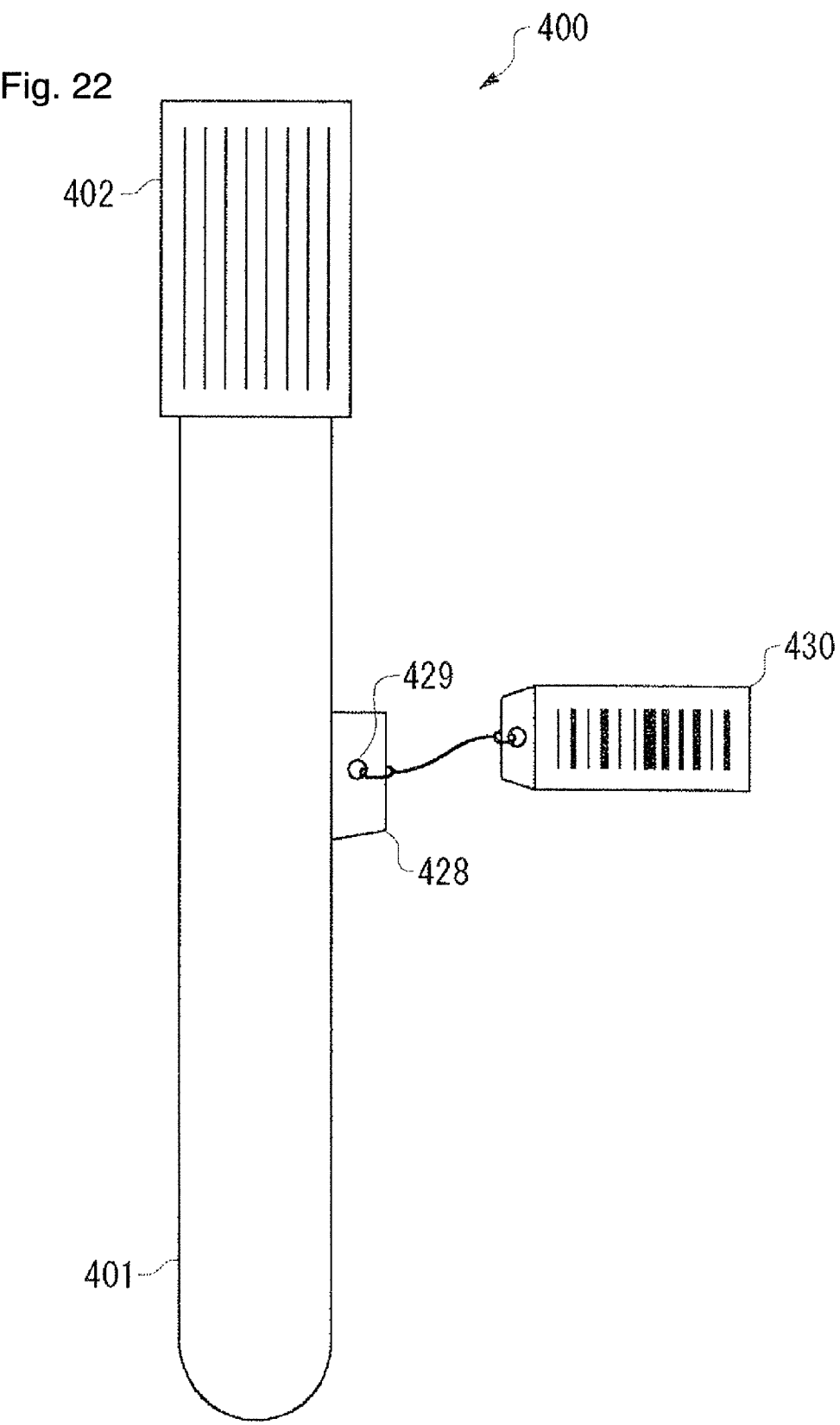
FIG. 22 is a plan view showing another modification of the vacuum blood collection tube in the fourth embodiment.

FIG. 22 is a plan view showing another modification of the vacuum blood collection tube 400 in the fourth embodiment. In this modification, a plate-like piece 428 is provided on the bottomed tube 401, and a tag attachment hole 429 is provided in the plate-like piece 428. A bar code tag 430 is attached to this tag attachment hole 429. When the plate-like piece 428 having such a tag attachment hole 429 is used, the bar code tag 430 can be easily attached to the bottomed tube 401.

According to such a vacuum blood collection tube 400 in the fourth embodiment, the amount of the collected blood sample can be easily measured by using the scale 424 of the bottomed tube 401.

Also, in this embodiment, using the affixing guide portion 425 as a reference, the sample identification mark seal (for example, the bar code seal 427) can be easily affixed along the predetermined affixing direction (for example, the axial direction of the bottomed tube 401).

Fifth Embodiment

Next, a vacuum blood collection tube in the fifth embodiment of the present invention will be described using FIG. 23 to FIG. 25. Here, description is given focusing on points where the vacuum blood collection tube in this embodiment is different from that in the third embodiment. Therefore, unless otherwise specified here, the configuration of this embodiment is similar to that of the third embodiment.

FIG. 23 is a plan view of the vacuum blood collection tube (a bottomed tube and a cryopreservation cap) in the fifth embodiment. As shown in FIG. 23, the bottom portion 504 of a bottomed tube 501 is composed of a cylindrical free-standing bottom part 524 and an inverted conical, concave bottom part 525. The free-standing bottom part 524 is formed in a cylindrical shape to support the bottomed tube 501, to which a cryopreservation cap 503 attached, so that the bottomed tube 501 can be free-standing. Also, the concave bottom part 525 is formed in an inverted conical shape so that a sample is gathered in the central portion when the amount of the sample decreases.

A vacuum blood collection tube 500 is usually placed vertically in a stand and handled. But, in a case where the bottomed tube 501 is used for cryopreservation, the operation is easy if the bottomed tube 501 is temporarily placed vertically using the free-standing bottom part 524, for example, when a bar code is checked. Also, in an operation with a syringe, the sample accumulated in the concave bottom part 525 can be collected without being left, so that the operation can be efficient. The shape of the concave bottom part 525 may be, for example, inverted conical, inverted pyramidal, inverted hemispherical (domed), or the like.

Figure 24:
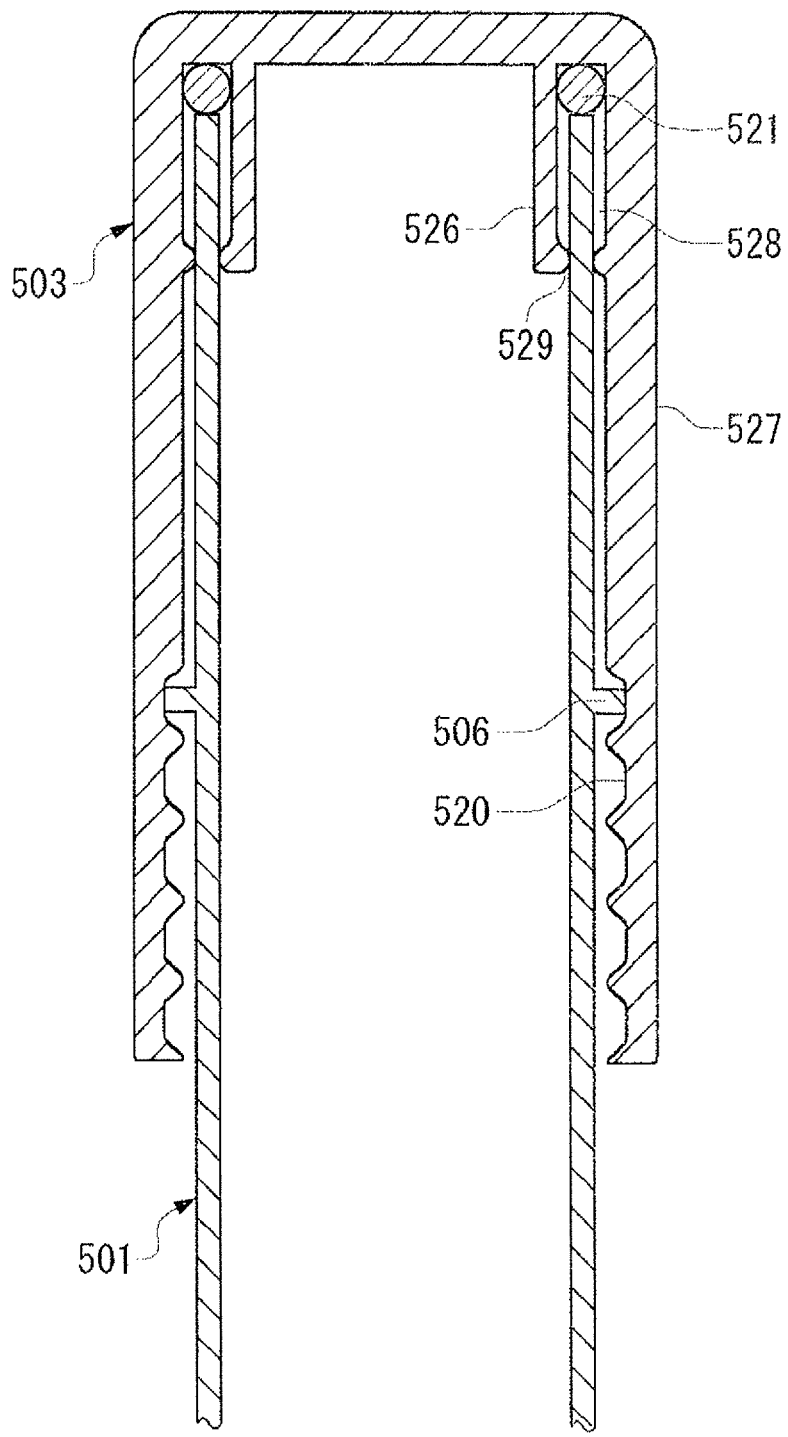
FIG. 24 is an enlarged cross-sectional view showing the rim locking structure of the bottomed tube and the cryopreservation cap.

FIG. 24 is an enlarged cross-sectional view showing the rim locking structure of the bottomed tube 501 and the cryopreservation cap 503. As shown in FIG. 24, a cylindrical inner cylinder 526 is vertically provided inside the cryopreservation cap 503, and an annular housing portion 528 is provided between the outer main body 527 and the inner cylinder 526 of the cryopreservation cap 503. The other end of the bottomed tube 501 is inserted into this annular housing portion 528. In other words, it can also be said that the cryopreservation cap 503 comprises the annular housing portion 528 having a clearance into which the other end of the bottomed tube 501 is inserted.

An O-ring 521 is fitted into the deep portion of this annular housing portion 528 (the upper portion in FIG. 24). Also, a projecting portion is provided on both sides of the inlet portion of this annular housing portion 528 (the lower portion in FIG. 24). It can also be said that a pinch portion 529 in which the width of the clearance is smaller than the thickness of the bottomed tube 501 is provided in the annular housing portion 528 by these projecting portions. This pinch portion 529 may be anywhere in the annular housing portion 528, and the pinch portion 529 in which the width of the clearance is smaller than the thickness of the bottomed tube 501 may be provided in a part where the annular housing portion 528 is bonded to a lid.

In this embodiment, by pinching the other end of the bottomed tube 501 by the pinch portion 529 of the annular housing portion 528, the outflow of a liquid (sample) from inside the bottomed tube 501, or the inflow of a liquid (liquid nitrogen or the like) from outside the bottomed tube 501 is prevented. In other words, by pinching the other end of the bottomed tube 501 by the pinch portion 529 of the annular housing portion 528, the liquid tight state of the bottomed tube 501 is maintained. Also, in this case, the O-ring 521 is attached to the deep portion of the annular housing portion 528, so that the liquid tightness of the bottomed tube 501 is improved.

Figure 25:
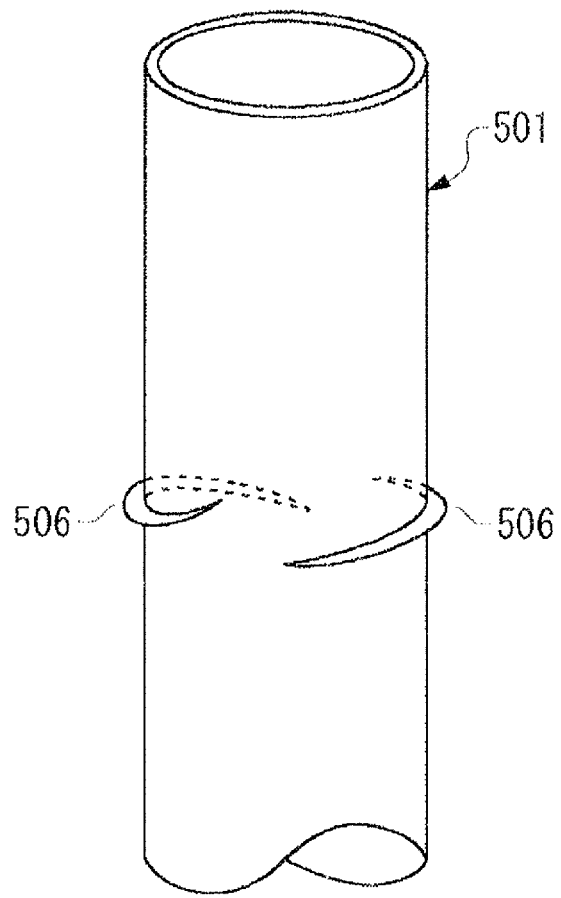
FIG. 25 is a perspective view showing the double thread of the bottomed tube.

FIG. 25 is a perspective view showing the double thread of the bottomed tube 501. As shown in FIG. 25, the thread portion 506 of the bottomed tube 501 is a double thread, and the thread groove portion 520 of the cryopreservation cap 503 is also a double thread (see FIG. 24).

The double thread is a thread having two thread start portions, as shown in FIG. 25. In the double thread, the play of the thread and the thread groove is equal on both sides, compared with a single thread. Therefore, the bottomed tube 501 and the cryopreservation cap 503 are in horizontal contact with each other, so that adhesion between both is enhanced.

Also, in the double thread, the lead is twice the pitch, so that the amount of rotation when tightening the thread is only half, compared with a single thread. Therefore, the bottomed tube 501 and the freezing and preservation cap 503 can be firmly fastened, and the operability when tightening the thread is high.

Here, the case where the thread portion 506 of the bottomed tube 501 and the thread groove portion 520 of the cryopreservation cap 503 are double threads is illustrated, but the present invention is not limited to this, and the thread portion 506 of the bottomed tube 501 and the thread groove portion 520 of the cryopreservation cap 503 may be multiple threads that are triple or more threads.

According to such a vacuum blood collection tube 500 in the fifth embodiment, the bottomed tube 501 can be temporarily placed vertically using the free-standing bottom part 524, so that the trouble of using a stand for placing the bottomed tube 501 vertically is eliminated, and the operability is improved. Also, the sample is accumulated in the concave bottom part 525, so that even if the amount of the sample decreases, the remaining sample can be easily removed by a syringe or the like, and the operability is improved. The concave shape includes, for example, an inverted conical shape, an inverted pyramidal shape, an inverted hemispherical shape (dome shape), and the like.

Also, in this embodiment, when the cryopreservation cap 503 is attached to the bottomed tube 501, the other end of the bottomed tube 501 is pinched in the pinch portion 529 of the annular housing portion 528, so that the liquid tight state of the bottomed tube 501 can be maintained.

Also, in this embodiment, the thread portion 506 of the bottomed tube 501 and the thread groove portion 520 of the cryopreservation cap 503 are in contact with each other at two places, and force is equally applied to both. Therefore, the cryopreservation cap 503 can be tightly threadedly attached to the bottomed tube 501, so that the liquid tightness of the bottomed tube 501 is improved. Also, in the double thread, the lead is twice the pitch, so that the amount of rotation when threadedly attaching the cryopreservation cap 503 to the bottomed tube 501 is only half, therefore, the tightening operation is easy, and the operability is improved.

(Method of Manufacturing Cryopreservation Cap of Vacuum Blood Collection Tube)

Figure 26:
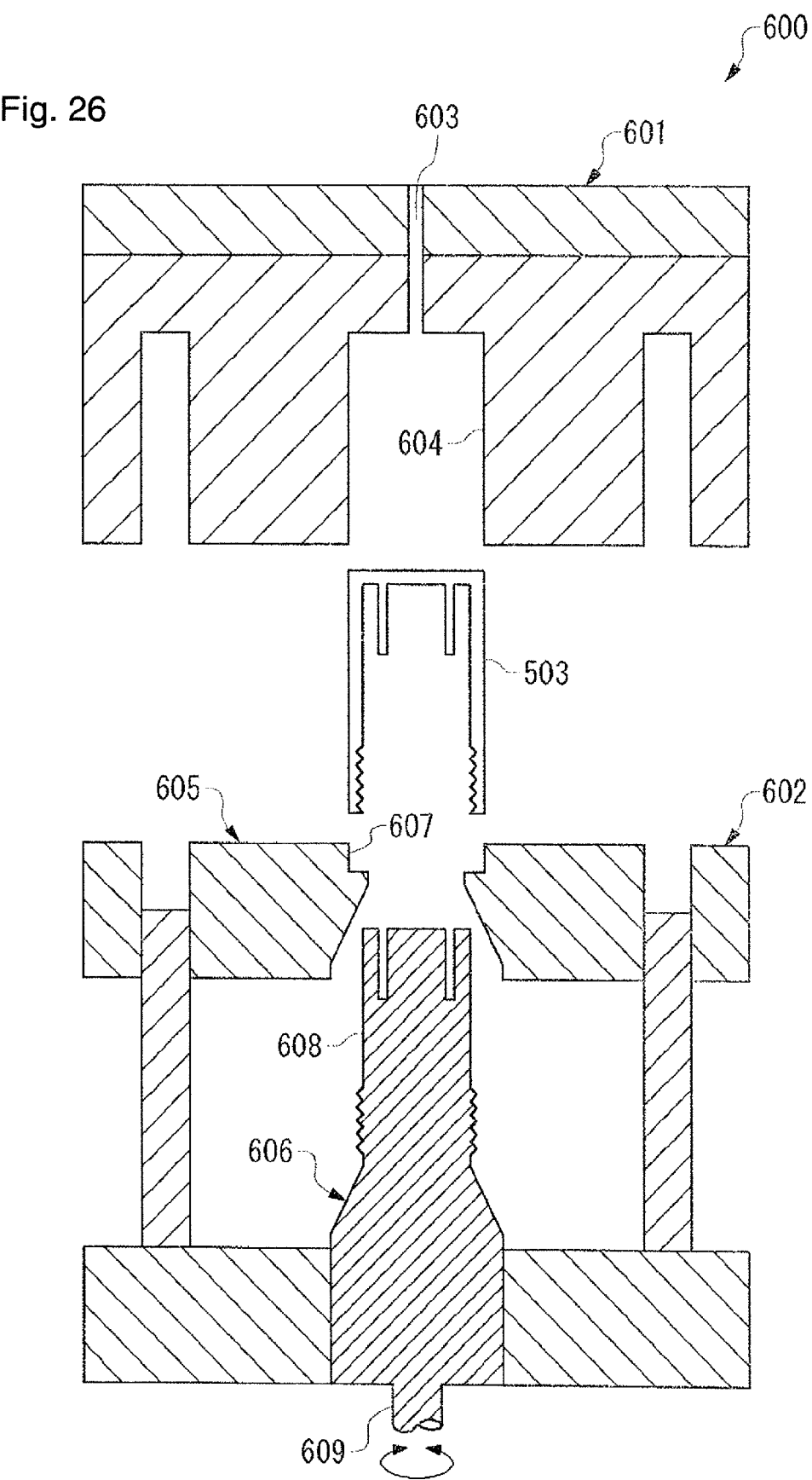
FIG. 26 is an explanatory view of a mold for manufacturing the cryopreservation cap of the vacuum blood collection tube.

Lastly, a method of manufacturing the cryopreservation cap of a vacuum blood collection tube will be described using FIG. 26 and FIG. 27. Here, a case where the cryopreservation cap in the fifth embodiment is manufactured will be described as one example. FIG. 26 is an explanatory view of a mold for manufacturing the cryopreservation cap of a vacuum blood collection tube, and FIG. 27 is an enlarged view of the cavity of the mold.

Figure 27:
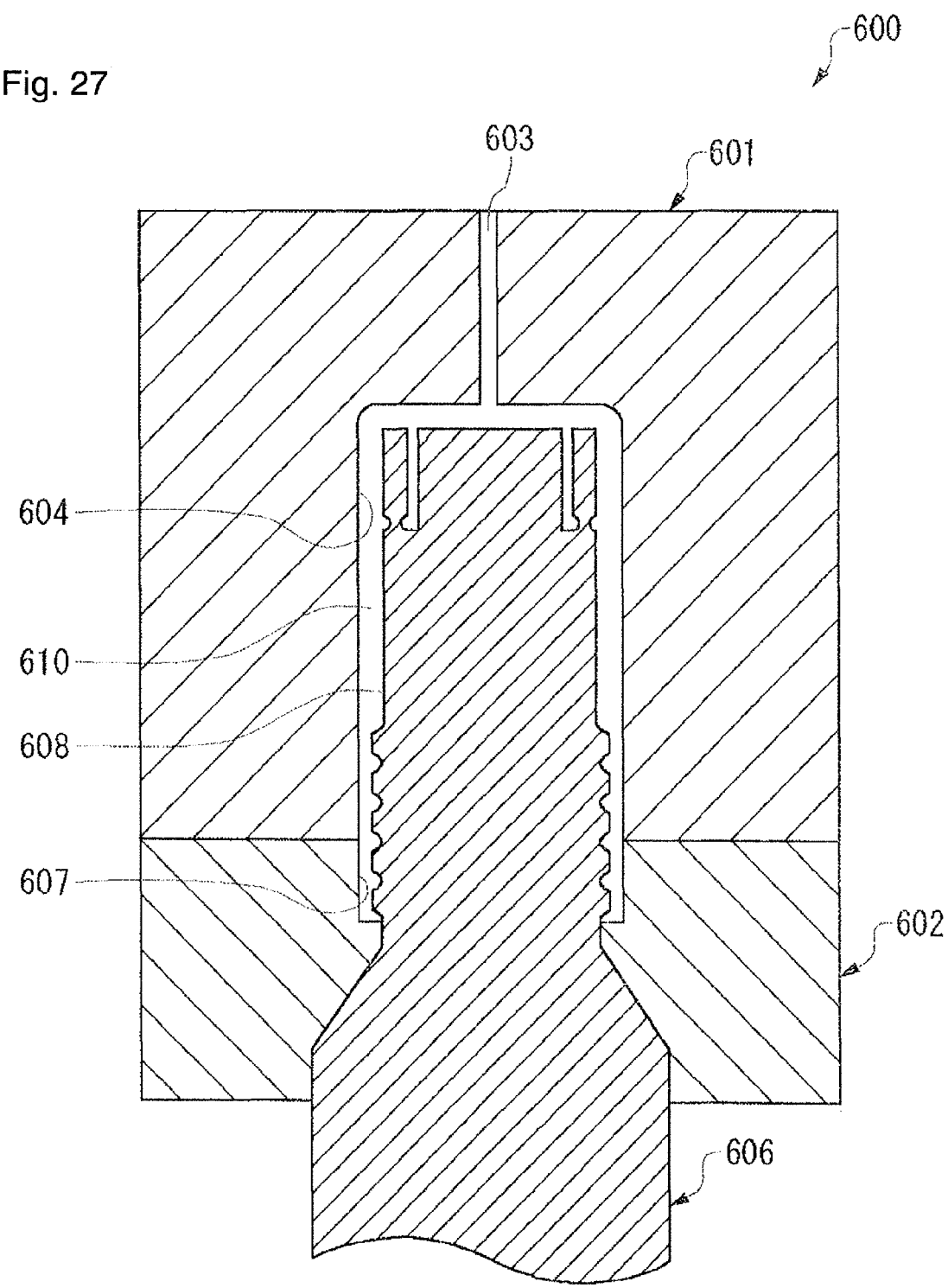
FIG. 27 is an enlarged view of the cavity of the mold.

As shown in FIG. 26 and FIG. 27, when the cryopreservation cap 503 of the vacuum blood collection tube is manufactured, a mold 600 composed of a fixed mold 601 and a movable mold 602 is used. The fixed mold 601 has a molding surface 603 corresponding to the shape of the outer periphery of the cryopreservation cap 503, and a resin injection port 604 for injecting a melted resin. The movable mold 602 is composed of an outer mold 605 and an inner mold 606. The outer mold 605 has a molding surface 607 corresponding to the shape of the outer periphery of the cryopreservation cap 503 and can be moved up and down with respect to the fixed mold 601. The inner mold 606 has a molding surface 608 corresponding to the shape of the inner periphery of the cryopreservation cap 503 and can be rotated around a rotation axis 609.

When the cryopreservation cap 503 of the vacuum blood collection tube is manufactured, first, the mold 600 (the fixed mold 601 and the movable mold 602) is clamped to form a cavity 610 having the shape of the cryopreservation cap 503. Then, a heated and melted low temperature resistant material is injected from the resin injection port 604.

Then, the low temperature resistant material is cooled and solidified, and then, the mold 600 is opened. In this case, the inner mold 606 of the movable mold 602 is rotated around the rotation axis 609 and moved downward with respect to the fixed mold 601, and the outer mold 605 of the movable mold 602 is moved downward with respect to the fixed mold 601. Thus, when the mold 600 is opened to remove a molding (the cryopreservation cap 503), the inner mold 606 of the movable mold 602 is pulled out, while being rotated, to form the thread groove portion 520 on the inner peripheral surface of the cryopreservation cap 503.

According to such a manufacturing method, the cryopreservation cap 503 can be manufactured in one step by molding, so that the manufacture of the vacuum blood collection tube is easy.

The embodiments of the present invention have been described by way of illustration, but the scope of the present invention is not limited to these, and changes and modifications can be made within the scope described in the claims according to the purpose.

In the above description, the case where the same low temperature resistant material is used for the bottomed tube and the cryopreservation cap of the vacuum blood collection tube is illustrated by an example, but the scope of the present invention is not limited to this. When the thermal shrinkage rate during cooling is generally the same, different low temperature resistant materials may be used for the bottomed tube and the cryopreservation cap.

Also, in the above description, the case where with the cryopreservation cap being a fitted-on type, the thread portion is provided on the outer peripheral surface of the bottomed tube, and the thread groove portion is provided on the inner peripheral surface of the cryopreservation cap is illustrated by an example, but the scope of the present invention is not limited to this. For example, the thread groove portion may be provided on the outer peripheral surface of the bottomed tube, and the thread portion may be provided on the inner peripheral surface of the cryopreservation cap. Also, with the cryopreservation cap being a threaded-in type (insertion type), the thread groove portion may be provided on the inner peripheral surface of the bottomed tube, and the thread portion may be provided on the outer peripheral surface of the cryopreservation cap. Further, when the cryopreservation cap fits suitably to the bottomed tube, the thread portion and the thread groove portion need not necessarily be provided.

Also, in the above description, the case where the cover is attached to the attachment portion of the cryopreservation cap is illustrated by an example, but the scope of the present invention is not limited to this. The cover need not necessarily be attached to the attachment portion of the cryopreservation cap.

The preferred embodiments of the present invention conceived now have been described, but it is understood that various modifications can be made to these embodiments, and it is intended that the appended claims encompass all such modifications within the true spirit and scope of the present invention.

INDUSTRIAL APPLICABILITY

As described above, the vacuum blood collection tube according to the present invention has the effect that the collected blood sample can be cryopreserved at ultra-low temperature as it is, without being transferred to another blood storage container, so that effort and burden on the operator can be significantly reduced. The vacuum blood collection tube according to the present invention is useful as a vacuum blood collection tube for cryopreserving blood for a long period for DNA analysis or the like.

The invention claimed is:
1. A vacuum blood collection tube comprising:
a bottomed tube which is composed of a low temperature resistant material that is less susceptible to low temperature fracture when cryopreserved at an ultra-low temperature of −40 degree Celsius to −200 degree Celsius and is thereby suitable for storage at an ultra-low temperature in the range of −40 degree Celsius to −200 degree Celsius; the bottomed tube having a bottom portion at one end and an opening at the other end;
a stopper which is attached to the opening of the bottomed tube before blood collection; which is in close contact with the opening of the bottomed tube so that a reduced pressure state inside the bottomed tube can be maintained, wherein pressure of said reduced pressure state is lower than atmospheric pressure; the stopper having a needle piercing portion composed of a rubber material that can be pierced with a blood collection needle; and
a cryopreservation cap which is composed of the low temperature resistant material that is less susceptible to low temperature fracture when cryopreserved at an ultra-low temperature of −40 degree Celsius to −200 degree Celsius and is thereby suitable for storage at an ultra-low temperature in the range of −40 degree Celsius to −200 degree Celsius; which is attached to the opening of the bottomed tube after blood collection; the cryopreservation cap sealing the opening of the bottomed tube under a condition of the ultra-low temperature so that a liquid tight state of the bottomed tube can be maintained.

2. The vacuum blood collection tube according to claim 1, wherein the cryopreservation cap is attached to the opening of the bottomed tube, in exchange of the stopper, after blood collection.

3. The vacuum blood collection tube according to claim 1, wherein the stopper comprises:
   a needle piercing member which is attached to the opening of the bottomed tube before blood collection; the needle piercing member being composed of a rubber material that can be pierced with a blood collection needle, and
   a cap member which is attached to the opening of the bottomed tube over the needle piercing member before blood collection; the cap member bringing the needle piercing member into close contact with the bottomed tube so that a reduced pressure state inside the bottomed tube can be maintained.

4. The vacuum blood collection tube according to claim 1, wherein a tube side thread portion is provided on a surface of the bottomed tube, and a cap side thread portion threadedly engaged with the tube side thread portion is provided on a surface of the cryopreservation cap, and wherein the cryopreservation cap is threadedly attached to the bottomed tube after blood collection.

5. The vacuum blood collection tube according to claim 4, wherein the tube side thread portion and the cap side thread portion are multiple threads.

6. The vacuum blood collection tube according to claim 4, wherein the tube side thread portion is a thread portion provided on an outer peripheral surface of the bottomed tube, and wherein the cap side thread portion is a thread groove portion provided on an inner peripheral surface of the cryopreservation cap.

7. The vacuum blood collection tube according to claim 6, wherein a thread absent portion in which the thread portion is not present is provided on the outer peripheral surface of the bottomed tube at a position on an opening side from the thread portion, and wherein the stopper is attached to the thread absent portion.

8. The vacuum blood collection tube according to claim 1, wherein the cryopreservation cap comprises an attachment portion to which a sample identification mark for identifying a collected blood sample is attached.

9. The vacuum blood collection tube according to claim 1, wherein a thin film having a gas barrier property is formed on an inner peripheral surface of the bottomed tube.

10. The vacuum blood collection tube according to claim 1, wherein a blood coagulation preventing agent for preventing coagulation of collected blood is placed in the bottomed tube.

11. The vacuum blood collection tube according to claim 1, wherein the low temperature resistant material is a cyclic olefin copolymer.

* * * * *